(12) United States Patent
Gilger et al.

(10) Patent No.: US 9,613,445 B2
(45) Date of Patent: Apr. 4, 2017

(54) MEDICAL INFORMATION DISPLAY SYSTEMS AND METHODS

(71) Applicant: Medivu, Inc., Melbourne, FL (US)

(72) Inventors: Mike Gilger, Satellite Beach, FL (US); Pinaki Asher, West Melbourne, FL (US); Howard Murray, Indian Harbor Beach, FL (US)

(73) Assignee: MediVu, Inc., Melbourne, FL (US)

( * ) Notice: Subject to any disclaimer, the term of this patent is extended or adjusted under 35 U.S.C. 154(b) by 0 days.

(21) Appl. No.: 14/212,990

(22) Filed: Mar. 14, 2014

(65) Prior Publication Data

US 2014/0285490 A1 Sep. 25, 2014

Related U.S. Application Data

(60) Provisional application No. 61/782,947, filed on Mar. 14, 2013, provisional application No. 61/783,349, filed on Mar. 14, 2013, provisional application No. 61/782,371, filed on Mar. 14, 2013.

(51) Int. Cl.
*G06T 11/20* (2006.01)
*G06F 19/00* (2011.01)
*G06F 3/0481* (2013.01)

(52) U.S. Cl.
CPC ........ *G06T 11/206* (2013.01); *G06F 19/3406* (2013.01); *G06F 3/04817* (2013.01)

(58) Field of Classification Search
CPC .. G06F 19/322; G06F 19/327; G06F 19/3406; G06F 3/04817; G06F 3/0482; G06Q 50/24; G06Q 50/22; G06Q 30/0269; G09B 23/28; G06T 11/206
See application file for complete search history.

(56) References Cited

U.S. PATENT DOCUMENTS

| 2004/0119756 | A1* | 6/2004 | Kumhyr | G06F 9/4443 715/837 |
|---|---|---|---|---|
| 2007/0094045 | A1* | 4/2007 | Cobbs | G06F 19/327 705/2 |
| 2009/0265188 | A1* | 10/2009 | Lamy | G06F 3/04817 705/3 |
| 2011/0152882 | A1* | 6/2011 | Wenderow | A61B 5/7475 606/130 |
| 2014/0214446 | A1* | 7/2014 | Nusbaum | G09B 19/00 705/2 |

OTHER PUBLICATIONS

Heimo Muller et al., "Interactive Patient Records", Infomation Visualisation (IV), 2010 14th International Conference, IEEE, Piscataway, NJ, Jul. 26, 2010 (Jul. 26, 2010), pp. 252-257.

* cited by examiner

*Primary Examiner* — Todd Buttram
(74) *Attorney, Agent, or Firm* — Michael D. Lazzara, Esq.; Pletatragallo Gordon Alfano Bosick & Raspanti, LLP

(57) ABSTRACT

A computer implemented method of displaying a virtual patient chart. The method includes receiving data relating to a patient and generating, using a processor, a graphic representing at least one attribute related to a characteristic of the patient, wherein the generating uses a plurality of consistent visual modification rules that convey additional information to the graphic. The method also includes displaying the graphic on a virtual patient chart.

16 Claims, 30 Drawing Sheets

MALE

FEMALE

PEDIATRIC

ADOLESCENT

SENIOR

OBSERVATIONAL PATIENT

FIG. 6A

| Heart Failure |  | Surgical Care Improvement / Surgical Infection Prevention |  |
|---|---|---|---|
| Acute Myocardial Infarction (AMI) |  | Stroke |  |
| Pneumonia |  | Venous Thromboembolism (VTE) |  |
*FIG. 8*
| 32                    32 | 32                    25 | 32                     4 |
|---|---|---|
| Patient just checked in, LOS average of 32 hours for diagnostic code. | When LOS is almost over, timer bar turns yellow. | When average LSO is exceeded, background turns red, second number becomes count-up clock. |
*FIG. 10*

 Ultra Sound
 Cat Scan
 Physical Therapy
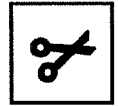 Surgery
*FIG. 12A*
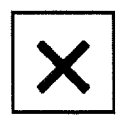 X-Ray
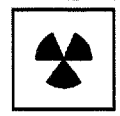 Nuclear Medicine
 MRI
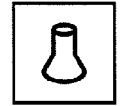 Other
*FIG. 12B*
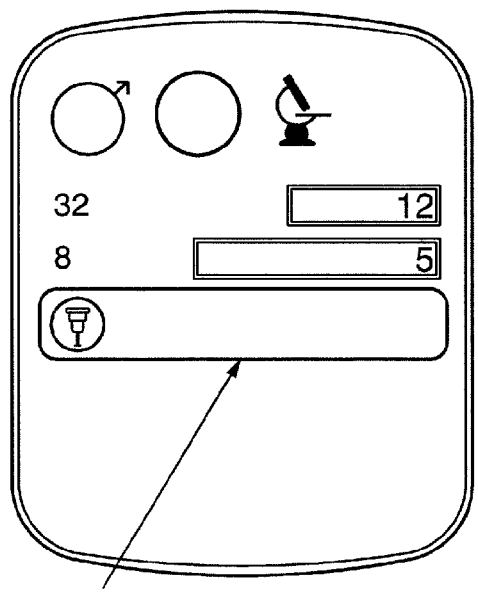
YELLOW OUTLINE
*FIG. 13A*
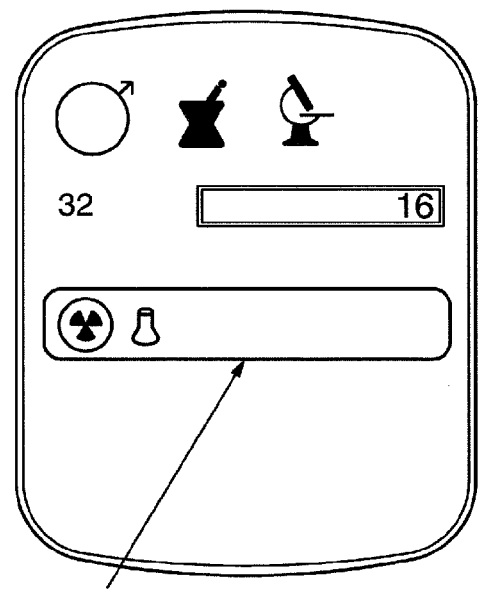
YELLOW OUTLINE
*FIG. 13B*

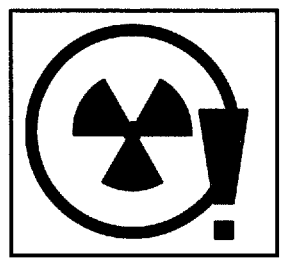 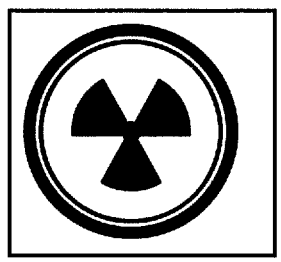
*FIG. 14A*  *FIG. 14B*
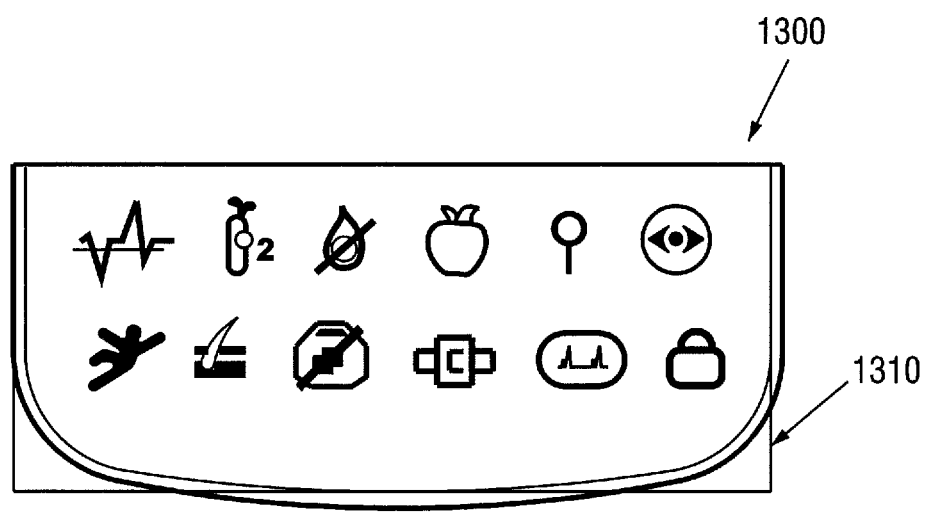
*FIG. 15*

White

Yellow

Red

RED SLASH

White

Yellow

MEDICAL INFORMATION DISPLAY SYSTEMS AND METHODS

CROSS REFERENCE TO RELATED APPLICATIONS

The instant application claims priority to U.S. Provisional Patent Application No. 61/782,947 filed Mar. 14, 2013, and U.S. Provisional Patent Application No. 61/783,349 filed Mar. 14, 2013, and U.S. Provisional Patent Application No. 61/782,371 filed Mar. 14, 2013.

BACKGROUND

The human brain processes visual images approximately 60,000 times faster than alphanumeric data. In healthcare environments, caregivers routinely pore through large amounts of data presented in alphanumeric format, which is a time-consuming process. Also, it is often difficult to correlate significant information from one report to the next and time constraints exist that may result in increased stress and may increase the chances of an error being made by a caregiver.

SUMMARY OF THE INVENTION

In a first aspect, embodiments of the invention provide a computer implemented method of displaying a virtual patient chart. The method includes receiving data relating to a patient and generating, using a processor, a graphic representing at least one attribute related to a characteristic of the patient, wherein the generating uses a plurality of consistent visual modification rules that convey additional information to the graphic. The method also includes displaying the graphic on a virtual patient chart.

In another aspect, embodiments of the invention provide a system. The system includes a database and a visual language engine in communication with the database, the visual language engine configured to: receive data relating to a patient from a medical system; generate a graphic representing at least one attribute related to a characteristic of the patient, wherein generating uses a plurality of consistent visual modification rules that convey additional information to the graphic; add the graphic to a virtual patient chart; and transmit the virtual patient chart to a display device.

In a further aspect, embodiments of the invention provide an apparatus. The apparatus includes means for receiving data relating to a patient, means for generating a graphic representing at least one attribute related to a characteristic of the patient, wherein the generating uses a plurality of consistent visual modification rules that convey additional information to the graphic; and means for displaying the graphic on a virtual patient chart.

In another aspect, embodiments of the invention are directed to a non-transitory computer readable medium including software for causing a processor to:

receive data relating to a patient;

generate a graphic representing at least one attribute related to a characteristic of the patient, wherein the generating uses a plurality of consistent visual modification rules that convey additional information to the graphic; and enable display of the graphic on a virtual patient chart.

BRIEF DESCRIPTION OF THE DRAWINGS

FIG. 6a illustrates an embodiment of a screen shot showing selection, or drill down on labs.

FIG. 8 illustrates six core measures that may be used on a shield according to various embodiments.

FIG. 10 illustrates embodiments of an LOS disotype in various stages.

FIGS. 12a and 12b illustrate embodiments of procedure disotype that may be displayed in the procedure notification area.

FIGS. 13a and 13b illustrate embodiments of examples of how procedure order status may be displayed on a shield.

FIGS. 14a and 14b illustrate embodiments of examples of affixes that may be used with procedure order disotypes.

FIG. 15 illustrates an embodiment of an example of a patient status area of a shield.

FIG. 21 illustrates an embodiment of a screen shot showing a detail screen of patient demographic information.

FIG. 22 illustrates an embodiment of a screen shot showing a detail screen of vital signs.

FIG. 24 illustrates an embodiment of a screen shot showing a detail screen of labs.

FIG. 26 illustrates an embodiment of a screen shot showing a detail screen of procedures.

FIG. 27 illustrates an embodiment of a screen shot showing a detail screen of procedures with further detail showing a procedure report.

DESCRIPTION

Figure 1:
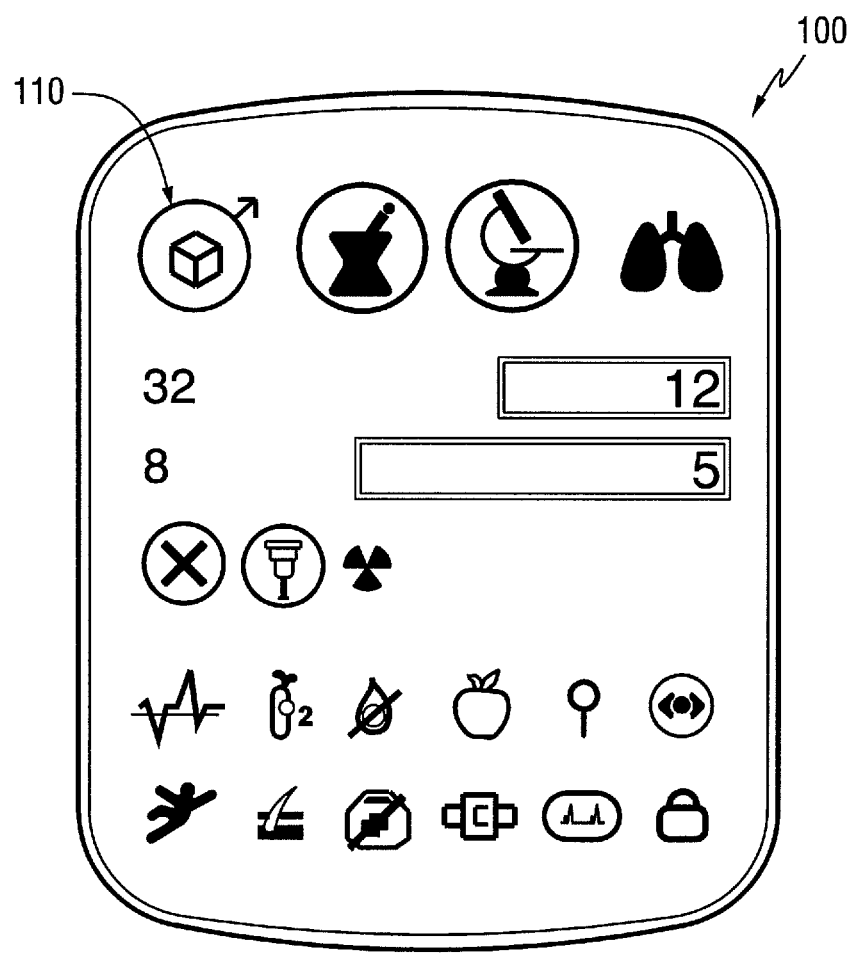
FIG. 1 illustrates an embodiment of an example of a visually communicated patient chart, or shield.

Various embodiments of the present invention are directed to methods, systems and devices for providing actionable patient information to users, such as caregivers, in an easy to grasp format to improve the quality of care and enhanced profitability. Embodiments are also directed to methods, systems and devices for displaying actionable patient information using a visual language, referred to as disotypes, to intuitively and accurately display large amounts of real time data related to the individual medical characteristics of a patient.

Various embodiments are directed to methods, systems and devices for presenting patient medical information in a standard way that reduces comprehension requirements and delivers more information per disotype on, for example, an information display screen. Embodiments also include methods, systems and devices for displaying information in the same visual field so that decisions and subsequent actions may be performed without changing screens to reduce cognitive load. Embodiments include displaying information organized by meaningful relationships to provide cognitive support to the user. Various embodiments are directed to methods, systems and devices for displaying patient status using disotypes to inform the user, for example at a glance, of any specific situational data that could impact the user's or a caregiver's decision making.

In display technologies, the cognitive strengths and weaknesses of the human mind may be taken into account such that visualization techniques exploit cognitive strengths to reduce cognitive loading so that higher-level problem-solving skills may be used more effectively. For example, the human brain has the ability to rapidly differentiate and process meanings for a specified set of shapes and colors. Thus, if a visualization technique can effectively present data utilizing shapes and colors, then the cognitive loading required between seeing and understanding data is reduced.

Many aspects of the human visual-processing system are automatic and other tasks can be performed at the same time because automation does not require use of conscious thought. In contrast, when interpreting presented data much uninterrupted attention must be applied when translating the data into thoughts, mostly conscious in nature, which reduces any simultaneous problem solving capacity. In various embodiments of the present invention, visualization techniques that use a system of graphics are presented. Such techniques remove the interpretation step of processing data such that the conscious thinking capability of the display operator can be applied directly to automatically understanding the visual representation of the data as it is being viewed.

Automatic visual processing may take place through "preattentive vision," which refers to those visual operations that can be performed prior to focusing attention on any particular region of an image. This ability allows users to perform certain types of visual analyses rapidly and accurately. This can include detection of specific elements with unique characteristics or patterns.

Embodiments of the present invention are directed to methods and systems for visual language display that use dynamic isotypes (referred to herein as "DI," or "disotypes") to display large amounts of real time data, or attributes, related to the individual medical characteristics of a patient. In various embodiments, disotypes are complete graphics that are comprised of various affixes that are rendered in whole or in part based on the dimensional metrics that the graphic is designed to convey. In various embodiments, the disotypes are positioned on a virtual chart, or shield, which acts to utilize the visual image processing capabilities of the brain.

Unlike with many visual paradigms that may map shapes, colors, and sizes to singular metrics with changing rules with no physical mapping of the image to the metric that it represents, disotypes are an embodiment of a visual language. As a language, in various embodiments disotypes employ logic and real-world references to convey, process, and assign meaning. Semantics may be used to express how meaning is inferred from the disotypes (analogous to words and sentences in the English language).

In various embodiments, disotypes have a system of rules (known as grammar) that govern the way disotypes communicate their intended meanings, and they may include morphology (the formation and composition of disotypes, which may be analogous to the formation and composition of words in the English language) and syntax (the formation and composition of phrases and overall meaning from the disotypes—which may be analogous to forming a sentence in the English language). In linguistics, morphology is the identification, analysis, and description of the structure of a given language's morphemes and other linguistic units, such as stems (base "words") and affixes.

In various embodiments, the lexicon for the visual language consists of disotypes and bound morphemes (sub-disotypes), which are the elements of the language that can't stand alone, like affixes, for example. An affix is a morpheme or sub-disotype that is attached to a base disotype—or stem—to form or express more meaning for that disotype. Placing several related disotypes together may allow the formation of an overall thought, or story, that conveys significant meaning to the "reader" of the language. A specific dialect of the language is specific to a knowledge domain. For example, a medial dialect is described herein in various embodiments.

As in the English language, the disotype is the main unit of the visual language syntax, and disotypes may be related to other disotypes by rules (grammars). Visual language users recognize these relations from their tacit knowledge of rules of disotype formation and they may infer intuitively that if a sub-disotype that is represented by a blue circle provides the meaning of "on order" for the disotype that represents medications, then if a blue circle sub-disotype is also applied to the disotype that represents laboratory tests, then that would mean that the lab test is "on order" due to the consistency of the semantics of the language.

In general, the grammars that represent the morphology of the language are what allow the human brain to "understand" that language, and to be able to read it without having to consciously think about the "words" that make up the language. The rules define specific patterns or regularities in the way disotypes are formed from smaller units in the language as well as how those smaller units interact to form a larger meaning. Words in a language are designed to represent a unit of meaning, and in a visual language, they represent a metric or a specific monitored "thing" or characteristic. The metrics or things or characteristics, may have multidimensional attributes (i.e, information that actively impacts the metric or thing or characteristic and which convey a greater meaning to the metric or thing or characteristic. For example, if the "thing" is the concept of "Labs" in the medical environment, there may be multiple associated attributes for Labs, such as: 1) are there labs on order?; 2) are any labs that were ordered "complete" yet?; 3) are any of the complete labs normal or abnormal?; 4) is there any history behind the labs?; 5) is the lab processing running behind?; and 6) are any of the labs ordered for immediate turnaround? Thus, for this single "thing" called "Labs", there may be six dimensions of data that are associated with Labs that provide far greater meaning for the current status of Labs, and current information visualization technologies, which are not based on language concepts, cannot display those multiple dimensions as a single "word." Also, such techniques cannot place several of those words (each with multidimensional attributes associated with the base) into an overall visual structure that represents sentences and that together tell an overall story of the underlying metrics.

In various embodiments, the dynamic attributes associated with the DI allow for more information to be displayed about that patient, including status and metrics. Embodiments allow a user, such as a caregiver, to more rapidly process and correlate large volumes of data regarding all of their patient's conditions and better determine priorities.

It can be understood that the user of the methods and systems described herein according to various embodiments may be any type of healthcare professional or healthcare administrator or clerical worker. Non limiting examples healthcare professionals are caregivers such as nurses and doctors. Although the following description uses examples such as laboratory orders, prescription orders, etc. in describing various embodiments, it should be understood that the teachings of such embodiments should not be limited to such examples, and embodiments of the invention are applicable to any type of information in the healthcare and other fields.

It can be understood that, although various aspects of the invention are described in connection with a hospital environment, the teachings of the embodiments described herein may be utilized in any acute, sub-acute, or ambulatory care environment such as hospitals, long-term care facilities, assisted living facilities, in home patient care, skilled nursing facilities, rehabilitation facilities, physician offices, clinics, outpatient surgery centers, nursing homes, laboratories, etc.

FIG. 1 illustrates an embodiment of an example of a visually communicated patient chart 100, referred to herein as a shield. As illustrated in the FIG. 1, embodiments of the present invention use graphics, styles, and conventions in displaying the shield. In various embodiments, the graphics, styles, and conventions are usability measures of efficiency, effectiveness, cognitive load and ease of learning. These measures provide for usability by way of an interface that is relatively easy to use and effective and is intuitive in that it allows a user to perform tasks quickly, efficiently and with a relatively low level of mental effort.

In various embodiments, dynamic disotypes utilize a consistent set of visual modification rules that convey additional meaning to the disotypes. When the rules are combined with the image processing power of the human brain, a user may reach conclusions about patient status relatively quicker than reading, for example, alphanumeric based data—thereby relieving stress, reducing time constraints, errors and costs and improving the quality of patient care. Various embodiments allow for a user to view multiple patients at the same time and to make decisions not only on a per-patient basis, but also for multiple patients.

In various embodiments, disotypes may include affixes called sub-disotypes that may be displayed with the base or stem disotype. For example, gender disotypes show two pieces of information—the gender of the patient and the general age grouping of the patient. As illustrated in FIG. 1, a gender disotype 110 uses the standard for the graphical representation for male and female. The disotype 110 also includes a further level of information—the age group of the patient. In various embodiments, the disotype affixes (the visual affix for the stem that creates a different or richer meaning) for age grouping may be pediatric, adolescent, and senior, and adult may be represented by having no disotype affixes affix displayed. The gender disotype 110 shown in FIG. 1 instantly shows the user that the patient is a male child in his adolescence.

In various embodiments, the communication interface of the present invention uses concepts, behavior, appearance and layout consistently to promote ease of use and a reduction in training requirements. Once a specific pattern in the way in which colors and graphics are utilized is learned by a user, that knowledge can be applied throughout, thereby reducing ongoing learning and creating a satisfactory comfort level for interaction with the system. Such an arrangement is possible due to the use of rules, as described hereinabove. The embodiments hereinbelow illustrate the use of rules to generate patient shields that display disotypes for various medical metrics or characteristics associated with a patient, such as lab orders, prescription orders, etc. As illustrated in such embodiments, a specific disotype may be fully represented as a graphic display of affixes. However, less than all of the affixes may be rendered in a disotype if the underlying data represented by the disotype is such that only a subset of the affixes affix needed to convey the intended meaning should be displayed.

Figure 2:
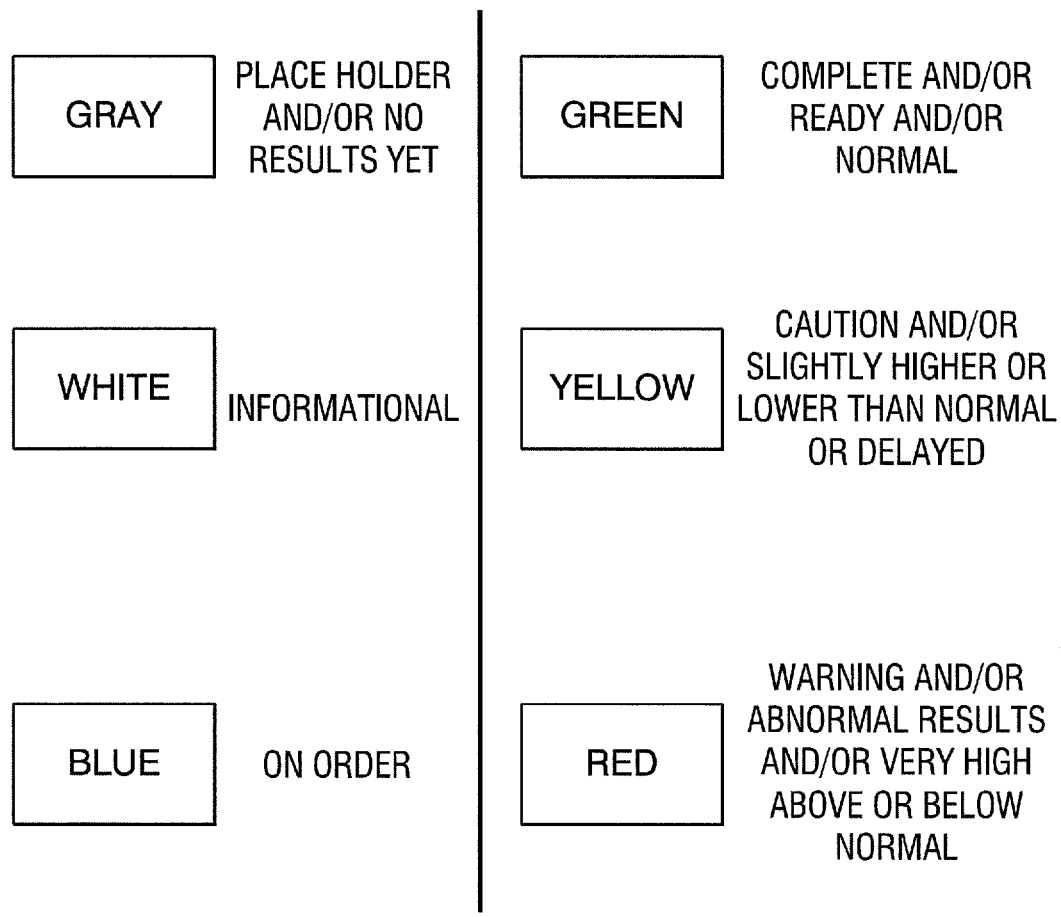
FIG. 2 illustrates an embodiment of a color scheme in which each color has a specific meaning.

In various embodiments, disotypes may use colors to provide a specific meaning syntax to the graphics. FIG. 2 illustrates a color scheme in which each color has a specific meaning. In various embodiments the meaning of each color stays consistent throughout its usage on the shield (i.e., the color becomes part of the syntax of the language). In the embodiments illustrated in FIG. 2, white means "informational;" green means "complete," "ready," and/or "normal;" blue means that there is a pending order such as a lab test or medical procedure; yellow is cautionary, or slightly above or below a normal value; and red is a warning and/or notification that results are above or below normal values by a certain threshold.

Figure 3A:
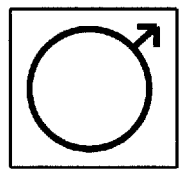
FIG. 3a illustrates an embodiment of a disotype for male patient.
Figure 3B:
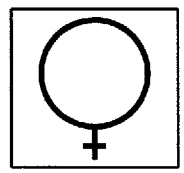
FIG. 3b illustrates an embodiment of a disotype for female patient.
Figure 3C:
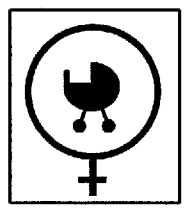
FIG. 3c illustrates an embodiment of a disotype for pediatric female patient.
Figure 3D:
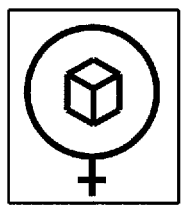
FIG. 3d illustrates an embodiment of a disotype for an adolescent female patient.
Figure 3E:
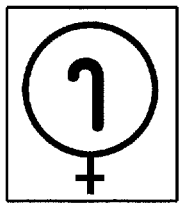
FIG. 3e illustrates an embodiment of a disotype for a senior female patient.
Figure 3F:
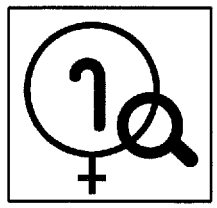
FIG. 3f illustrates an embodiment of a disotype for an observational female patient.

As shown in FIGS. 3a-3f, in various embodiments the gender disotype gives two pieces of information—the gender of the patient and the general age grouping of the patient. The disotype uses the standards for the graphical representation for male (FIG. 3a) and female (FIG. 3b). The gender disotype may be modified with a sub-disotype that gives the age grouping. Examples of sub-disotypes for age grouping are pediatrics (FIG. 3c); adolescent (FIG. 3d); and senior (FIG. 3e). The gender disotype may also have "affixes" that may be displayed with the disotype to give the caregiver more information about the disotype. Example affixes may be observational patient (FIG. 3f) and non-process based observational patient. The information may be used for decision making on, for example, orders, potential roommates in a shared room, etc.

Prescription and laboratory (lab) order disotype may be included in the shield 100 to indicate, for example, outstanding orders, completed orders, and orders being either normal or abnormal. In various embodiments, the user may select a disotype using, for example, a pointing device such as a mouse or by touching the disotype on a touch screen, to "drill-down," or display more information such as a list of all outstanding orders and their status.

Figure 4A:
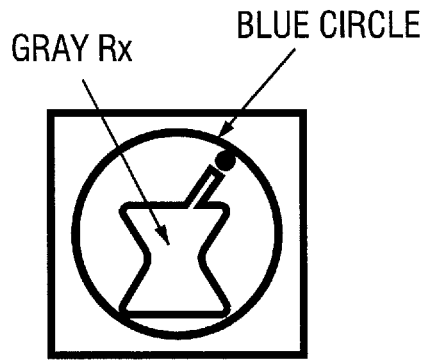
FIG. 4a illustrates an embodiment of a disotype for prescriptions pending with no orders currently complete.
Figure 4B:
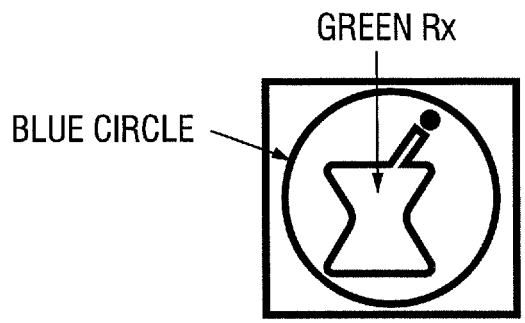
FIG. 4b illustrates an embodiment of a disotype for one or more prescription orders complete, but others still on order.
Figure 4C:
FIG. 4c illustrates an embodiment of a disotype when all of prescriptions have been filled.

As shown in FIG. 4a, a gray Rx disotype with a blue circle affix may represent that one or more prescription orders are in the system and not yet complete. As soon as one or more of the prescription orders are complete, the disotype may be rendered solid green to show that at least one prescription order has been delivered by the pharmacy. Because there may be multiple prescription orders that are not complete at the same time, a blue circle may be rendered as an affix of the green disotype as shown in FIG. 4b to designate that some of the orders are complete, but others are still being filled. The blue circle may also be used as an affix for a laboratory order disotype to show that some lab orders have been completed, but others are still outstanding. When all outstanding prescription orders are complete, the disotype may be rendered without the blue circle affix, and the green Rx disotype displays as shown in FIG. 4c. Such color circles affixes are consistently used with other disotype as described herein.

Figure 4D:
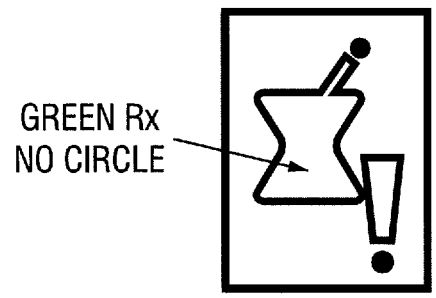
FIG. 4d illustrates an embodiment of a prescription indictor including a STAT affix.
Figure 4E:
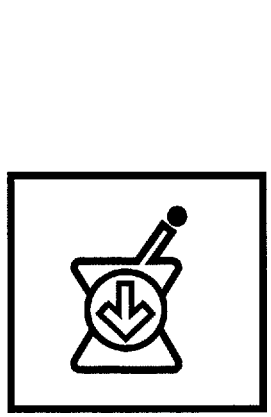
FIG. 4e illustrates an embodiment of a prescription disotype having an arrow disotype to show that all of the prescriptions have been acknowledged.
Figure 4F:
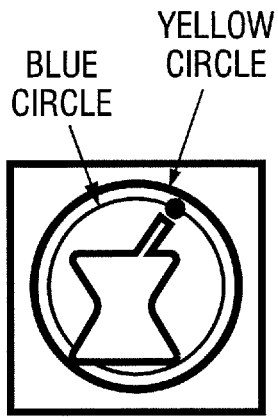
FIG. 4f illustrates an embodiment of a disotype showing one or more prescriptions are delayed.
Figure 4G:
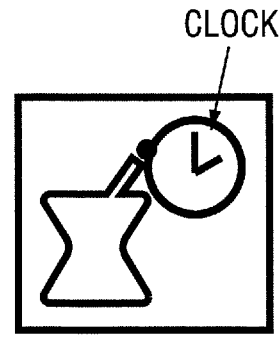
FIG. 4g illustrates an embodiment of a prescription disotype with a clock affix.

Another affix that may be incorporated into a disotype is the delayed prescription administration affix. In various embodiments, such an affix may be used by hospitals that support direct interfacing with prescription delivery and point-of-care data entry systems. Such systems may allow monitoring of when prescription medications have been administered and when they are due so that delays in time-based delivery may be rendered with an affix that is part of the disotype such as, for example, a clock affix as shown in FIG. 4g.

Figure 5A:
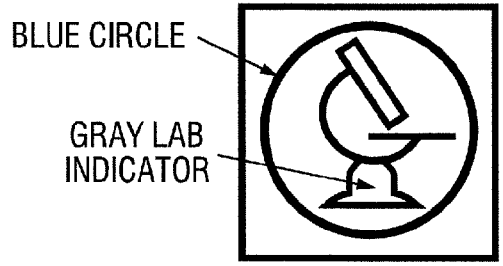
FIG. 5a illustrates an embodiment of a disotype showing lab results pending with no orders currently complete.
Figure 5B:
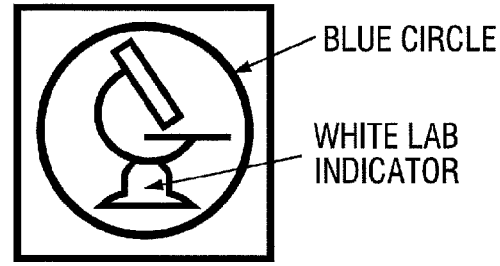
FIG. 5b illustrates an embodiment of a disotype showing some labs are complete but other labs are still on order.
Figure 5C:
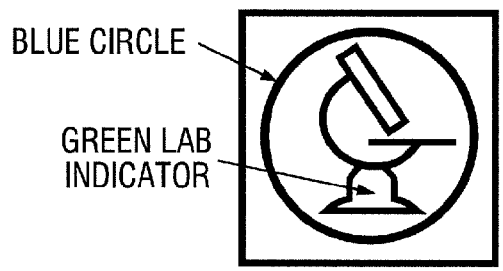
FIG. 5c illustrates an embodiment of a disotype for labs with all completed labs normal and with some labs still on order.
Figure 5D:
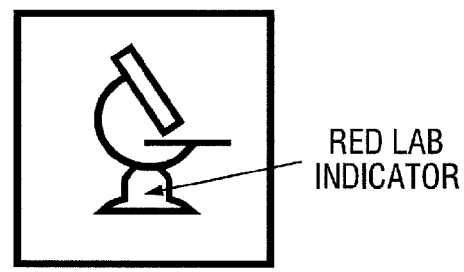
FIG. 5d illustrates an embodiment of a disotype that shows there are labs with one or more abnormal results.
Figure 6A:
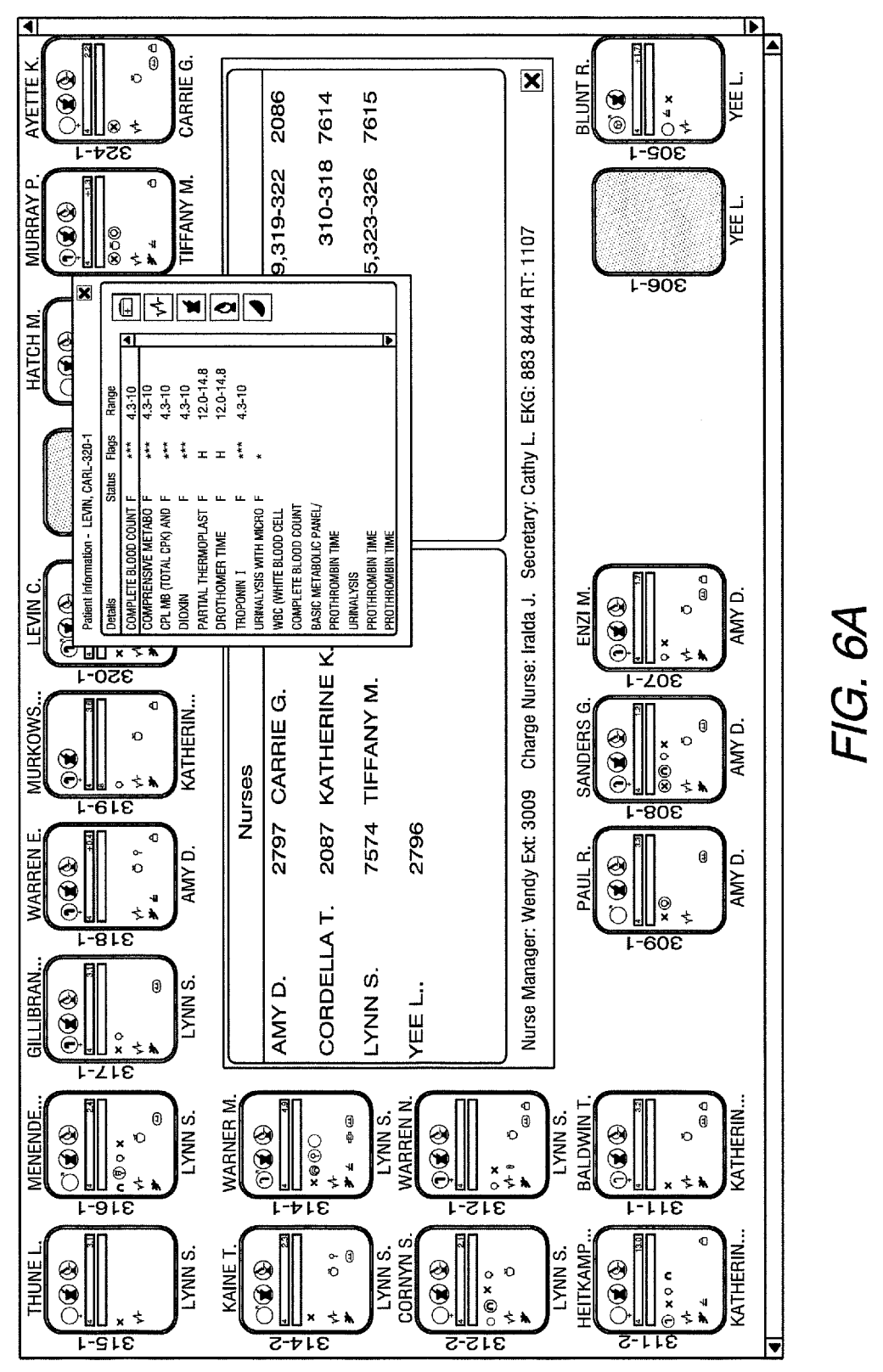
Figure 6B:
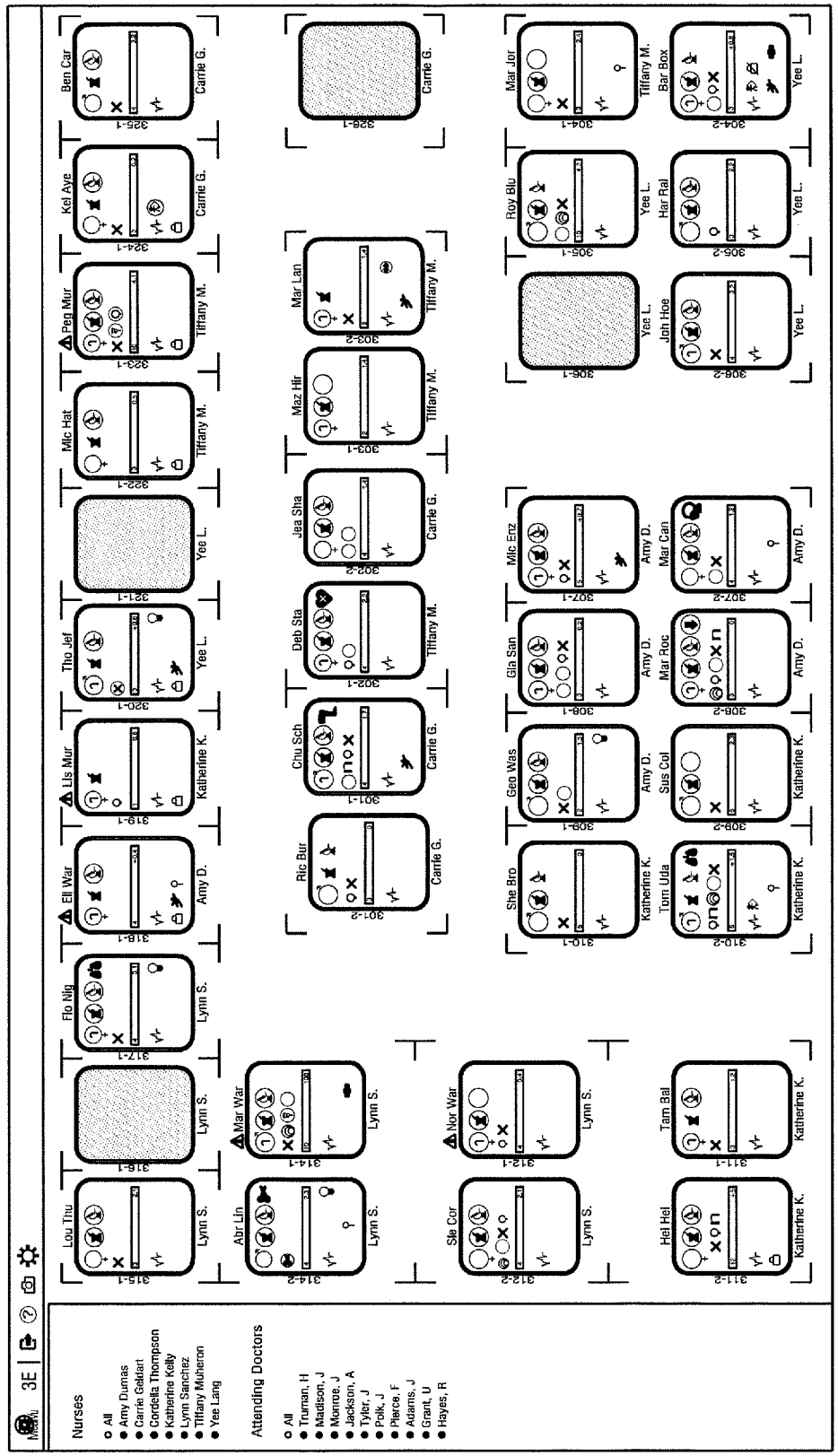
FIG. 6b illustrates an embodiment of multiple shields arrayed on a display screen.

FIG. 5a illustrates an embodiment of a gray lab disotype (represented by a microscope) with a blue circle affix rendered with it to represent that there are one or more labs on order, but none of the labs are complete yet. If the lab disotype turns white, green, or red with the blue circle affix, then this indicates that one or more of the tests have been completed, but others are still on order and not yet completed. When the lab disotype is white as shown in FIG. 5b, it is not known if the completed lab is normal or abnormal. When the lab disotype is green as shown in FIG. 5c, the results are all normal. When the lab disotype is red as shown in FIG. 5d, then the one or more of the tests came back with abnormal results. In various embodiments, the user may select the disotype to drill-down to the details of the labs as shown in FIG. 6a to view the results. If the blue circle affix is not rendered as shown in FIG. 5d, then all lab results are in, and the language syntax dictates that the color of the microscope disotype indicates the status of the results. It should be understood that the indictors shown in FIGS. 5a-5d are examples, and other colors may be incorporated into the language syntax to add other meanings to the disotypes and other disotype representations may be used. FIG. 6b illustrates an embodiment of multiple shields arrayed on a display screen.

For both the lab disotypes (FIGS. 5a-5d) and prescription disotypes (FIGS. 4a-4c) "affixes" may also be rendered with the disotype to display more information about the disotype. Examples of affixes are STAT for prescriptions as shown in FIG. 4d, orders acknowledged (FIG. 4e), order delayed (FIG. 4f), and time-based Rx administration (FIG. 4g).

The orders acknowledged affix first appears when a caregiver administers a prescription to the patient. The user may view a list of all the prescription orders, select one (or more) that have been administered, and "acknowledge" them. When orders are acknowledged, those orders no longer affect the prescription disotype colors. Any outstanding orders that have not yet been acknowledged may still impact the colors. In various embodiments, the orders that have been acknowledged show an arrow with the Rx as shown in FIG. 4e. The arrow informs the user that orders have been acknowledged, and that if they desire to view the acknowledged orders, they may select the arrow to view a list of orders and their statuses.

Figure 5E:
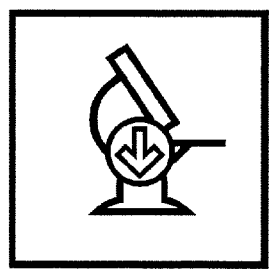
FIG. 5e illustrates an embodiment of a disotype showing all lab orders complete with no labs currently on order, and showing an arrow with a gray lab.

In various embodiments, the arrow affix may also apply to labs—once the lab results have been reviewed, the user may select labs they have reviewed, and the lab disotype will show that orders that have been acknowledged by being rendered with the arrow. If there are no more labs on order, and all labs have been acknowledged, then the arrow may be rendered on the gray lab disotype as shown in FIG. 5e.

The order delayed affix may show the user that for the orders currently outstanding (Rx, lab, procedure, etc.), one or more of the orders is taking longer than average to fulfill. FIG. 4f shows the disotype that may be used when one or more lab orders are delayed. The disotype uses a yellow circle affix to indicate that the order type that is delayed. The information may help caregivers remain cognizant of delays that may require further attention.

Figure 7:
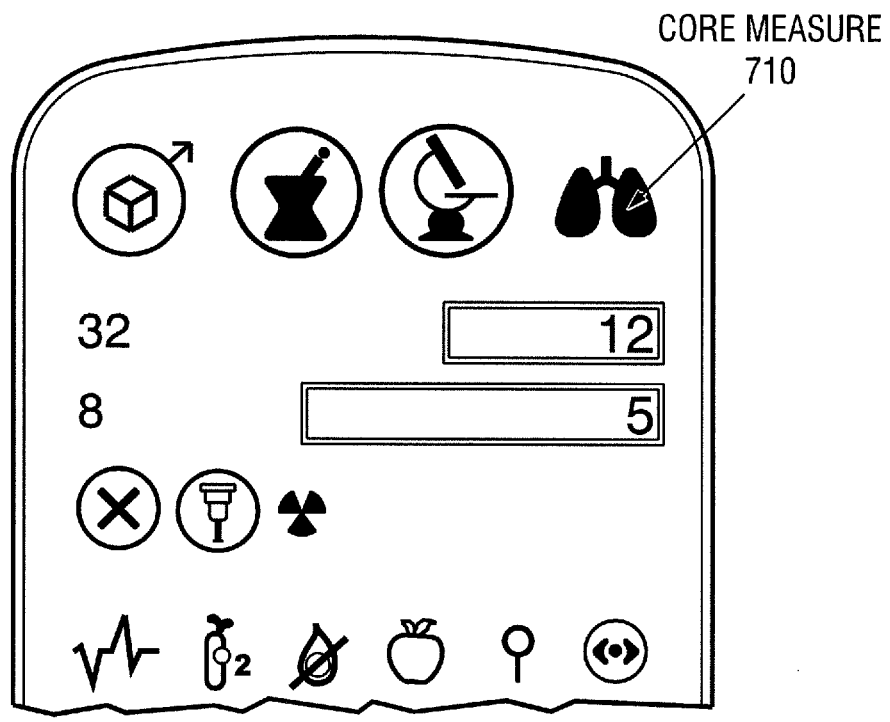
FIG. 7 illustrates an embodiment of a core measure disotype on a shield.

The shield illustrated in FIG. 7 shows a core measure disotype 710 that indicates to the user that the patient has a diagnostic code that is being measured under the Hospital Quality Alliance (HQA). No disotypes are displayed when the diagnostic code is not one that is being measured by the HQA. If active, the disotype is white because the communication is informative. FIG. 8 illustrates six core measures that may be used according to various embodiments. In various embodiments, when a user views the disotypes, the user may select the disotype to view a hospital approved list of measures.

Figure 9:
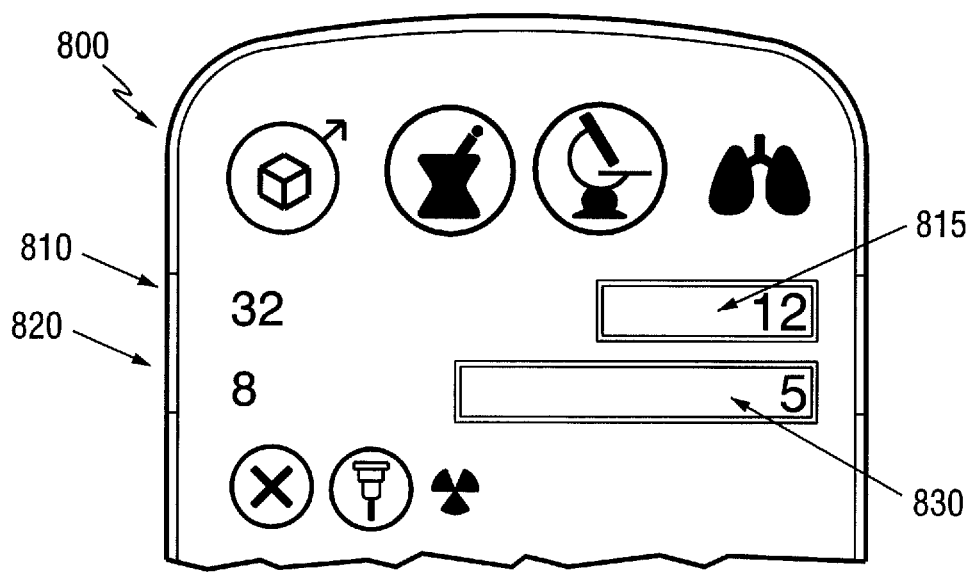
FIG. 9 illustrates an embodiment of length of stay (LOS) and discharge disotype on a shield.

Referring to FIG. 9, length of stay (LOS) disotype 810 and discharge disotype 820 may be displayed on a shield 800. The user may compare the LOS disotype 810 to the average LOS for a specific diagnostic code so that the user may see if the patient is far enough along in their treatment as compared to the average remaining time left on the LOS disotype 810. Using the discharge disotype 820, the user can see that, based on the amount of time left, all of the appropriate steps necessary to release the patient have been completed, ensuring no delays for the patient's discharge.

For the LOS countdown timer, the LOS disotype 810 represents the average LOS for a diagnostic code and a second number is a timer 815. Although the time indications herein are represented in hours, it may be understood that the time disotypes may be represented in any format using any combination of, for example, days, hours and minutes.

As illustrated in FIG. 10, when the timer 815 counts down to zero, it becomes a count-up timer, with the bar turning red to indicate that the average LOS has been exceeded. The discharge disotype 820 represents the total hours from time of order to the scheduled discharge, and a second number is a timer 830. In various embodiments, the timer 830 is hidden until a discharge order is issued.

Knowing the procedures that are on order may help a user such as a caregiver in managing the workflow surrounding the patient. For example, knowing that surgery or a significant (i.e., time consuming) test is scheduled may call for changes in the order and timing of treatments/preparations for the patient. Situation awareness of these items may extend the decision making capabilities of the caregivers and allow them to be more efficient and more prepared in the management of the overall care of the patient.

Figure 11A:
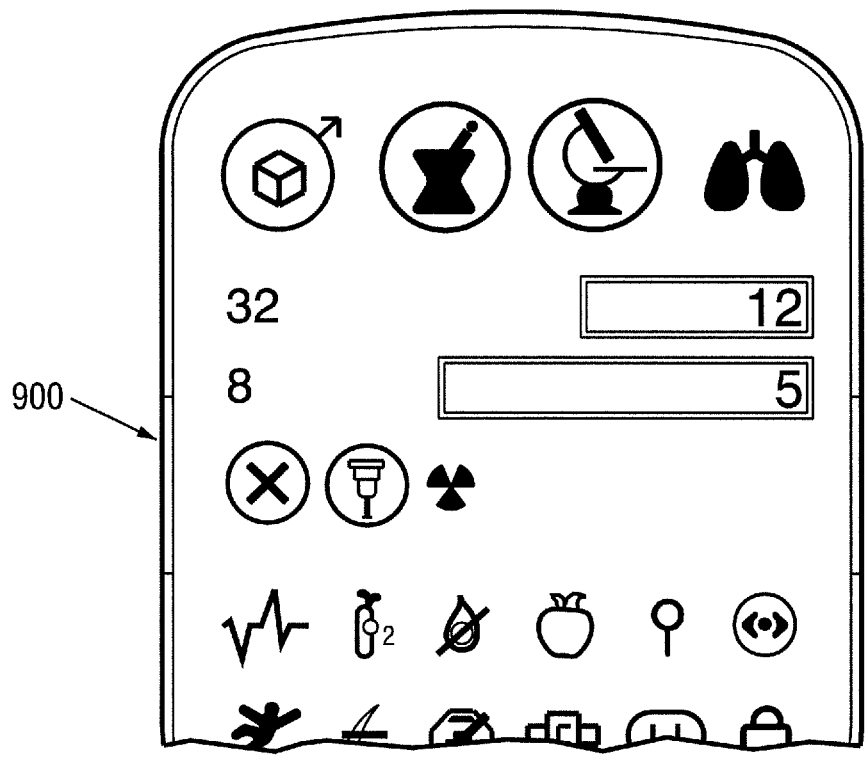
FIG. 11a illustrates an embodiment of a procedure notification area on a shield.

FIG. 11a illustrates an embodiment of a procedure notification area 900 on a shield. The procedure notification area 900 may be used to derive a probable location of a patient. As can be seen in FIG. 11a, the procedure notification area 900 may provide the ability (depending on the capability of the institution using the system) to ascertain the location of a patient if they are not currently in their room.

Figure 11B:
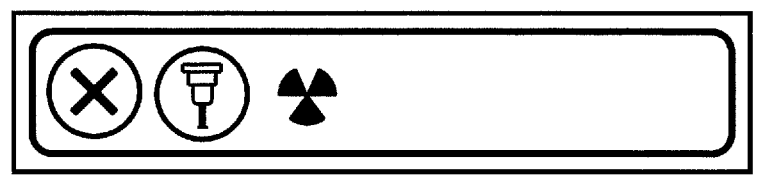
FIG. 11b illustrates an embodiment of a procedure notification area on a shield with a yellow outline.

If it is known that the patient is out of the room, a rectangle around the procedure notification area 900 may turn yellow as shown in FIG. 11b. In various embodiments an electronic patient movement system may communicate information to the system that informs the system that the patient has been moved from the room for a procedure. In various embodiments procedures that take a significant amount of time to "check-in" a patient (e.g., surgery, physical therapy, etc.) may communicate to the system that the patient is checking in at the location of the procedure. In various embodiments a radio frequency (RF) tag may be placed on the patient, and as the patient moves about the hospital, the system is notified of the movement and displayed on the shield.

FIGS. 12a and 12b illustrate procedure disotypes that may be displayed in the procedure notification area 900. If only one procedure is ordered, only that disotype is displayed. In various embodiments the disotypes are white in color, indicating that they are complete, but the result is unknown. In various embodiments, the color is displayed as green for a normal result or red for an abnormal result. Table 1 illustrates an example of a color scheme that may be used in displaying the disotypes.

TABLE 1

| disotype Color Scheme | |
|---|---|
| White | Test complete, normal/abnormal unknown |
| Green | Test complete, result normal |
| Red | Test complete, abnormal results |
| Gray | This color, coupled with a blue circle indicates that the test is on order, but not yet complete |

In the shields shown in FIGS. 13a and 13b a yellow outline denotes that the patient is out of the room. In FIG. 13a the patient has a PT order, and thus is most likely in that procedure. In FIG. 13b there is a nuclear test on order and an "other" test that is complete. The user may select the "other" test at any time to see the details of the order to determine what the actual test is. Because the patient is out of the room it can be deduced that their location would be one of the two labs that were ordered. In various embodiments, the background of the procedure location where the patient is turns white to indicate that the patient is currently having the procedure performed.

In various embodiments, the area 900 may allow for more accurate searches to determine the location of a misplaced chart when a patient returns to their room due to the fact that the area 900 displays the possible prior locations of the patient.

In various embodiments, the area 900 may display up to six procedure type disotypes. The disotypes may represent a procedure type, so that if there are multiple X-Ray procedures on order, only one X-Ray disotype shows up, and a drill down on the disotype shows all of the procedures on order and their current results. If more than six procedure types are ordered, an ellipse disotype may be displayed that allows the user to see that there are more types ordered so that the user may select the shield to view all active procedure orders for the patient.

In various embodiments the procedure notification area 900 supports two affixes—the STAT affix and the delayed affix. As in the lab and prescription cases described hereinabove, the STAT affix may use an exclamation point as shown in FIG. 14a.

Figure 16A:
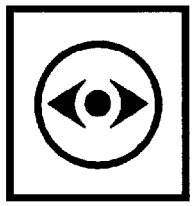
FIGS. 16a through 16l illustrate embodiments of different disotype that may be displayed in the patient status area shown in FIG. 15.
Figure 16B:
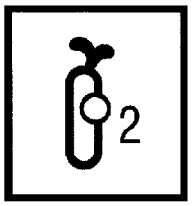
Figure 16C:
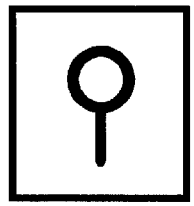
Figure 16D:
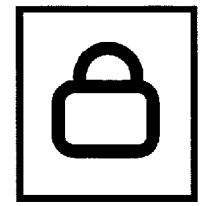
Figure 16E:
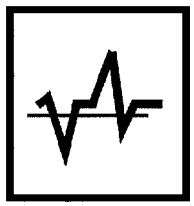
Figure 16F:
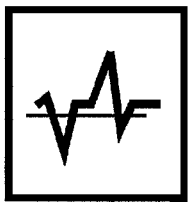
Figure 16G:
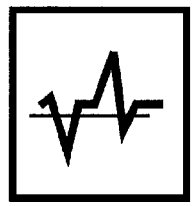

FIG. 15 illustrates an example of a patient status area 1310 of a patient shield 1300. FIGS. 16a-16l illustrate different disotypes that can be displayed in the patient status area 1310 shown in FIG. 15. The patient status area 1310 of the shield 1300 in FIG. 15 shows current patient status and may be used to inform the user of any specific situational data that could impact decision making. Such information may help the user make better decisions regarding, for example, patient preparatory requirements and caregiver work management. For example, if the patient watch disotype shown in FIG. 16a is present then a caregiver must be present with the patient at all times.

In various embodiments disotypes represent yes/no state information—e.g., is the patient on oxygen (FIG. 16b)?; is the patient diabetic (FIG. 16c)?; is the patient in isolation (FIG. 16d)? In various embodiments disotypes may display more information using colors or affixes to the disotype. An example of a disotype that uses color for more information is the vitals status disotype shown in FIGS. 16e-16g. The vitals status disotype informs the user of the current status of the patient's vital signs. If the patient's vital signs are within the normal healthy range, the disotype may be green. If the status of the patient's vital signs is not known, the disotype may be white (not shown). If the patient's vital signs are mildly above or below normal readings, the disotype may turn yellow, and the disotype may turn red if the vital signs are significantly above or below normal readings. The user may get the current details of the various vital readings by selecting the disotype and can immediately see which patients have readings that are not normal, as well as how far out-of-normal they are, which could impact decisions being made regarding particular patients.

Figure 16H:
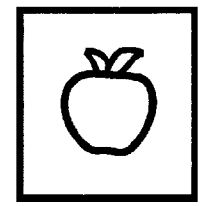
Figure 16I:
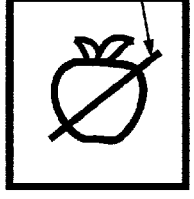
Figure 16J:
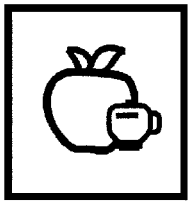
Figure 16K:
Figure 16L:
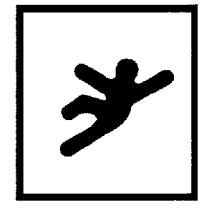
Figure 17:
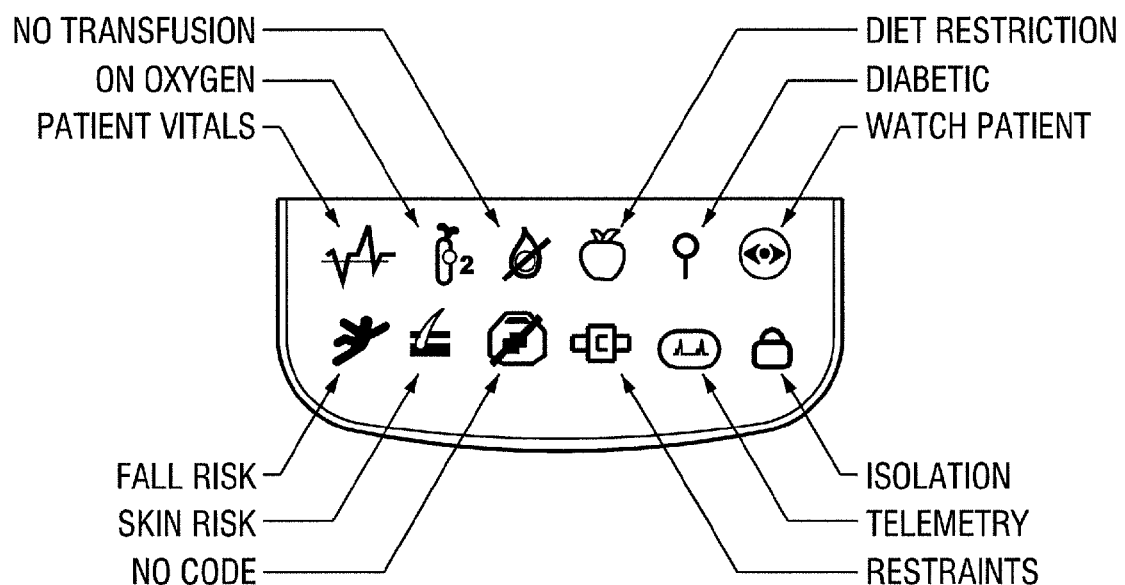
FIG. 17 illustrates an embodiment of various patient status disotype that may be used in the patient status area shown in FIG. 15.

Another example is the diet disotype shown in FIGS. 16h-16j. A plain apple informs the user that there is some form of diet restriction applied to the patient. However, in various embodiments there may be affixes for the disotype. For an NPO (nothing by mouth) order, a red slash may be displayed through the apple (FIG. 16i). If there is a caffeine restriction, a cup with a null may be displayed over the apple (FIG. 16j). Another example is a fall risk disotype shown in FIGS. 16k and 16l, which may be white for a patient with a fall risk (FIG. 16k), and may be yellow for a high-risk fall patient (FIG. 16l). FIG. 17 shows various patient status disotypes in a patient status area.

Figure 18:
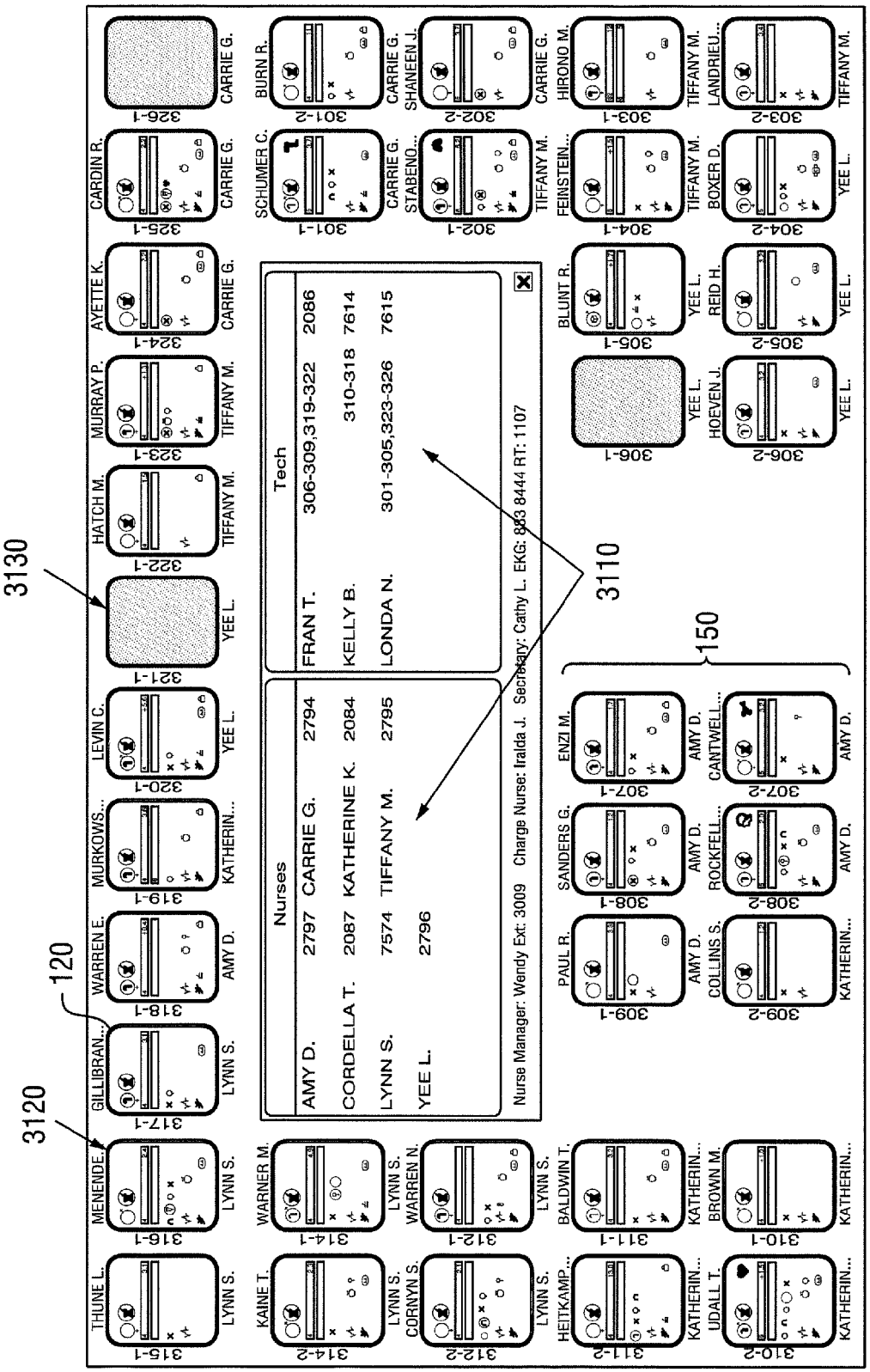
FIG. 18 illustrates an embodiment of a screen shot showing a layout of shields according to room assignment for a unit.

FIG. 18 illustrates an example of a display of a medical unit/ward in a hospital. The display shows a team of nurses and technicians 3110 that are identified by name and multiple patient rooms that are arranged in the same order as they are on the actual floor. Patient shields 3120 are arranged according to room location on the floor. Rooms that are empty are shown as blanks 3130 on the display screen.

As shown in FIG. 18, patient rooms are identified on the screen by room number starting with room 301 (right side) and ending with room 326 (above room 301). In the example illustrated in FIG. 18, rooms can be single rooms such as 120 as indicated by the -1 added to the room number or double rooms such as 150 indicated by -1 and -2 to show which bed each particular patient occupies in the room. The displayed information also includes patient names shown above the patient shields and the nurse assigned to each patient is displayed below the shield. For example, room 315-1 (upper left corner) is a single room, the patient's name is Thune and nurse Lynn is assigned to the patient. When two or more patients have the same name, the names may be highlighted in, for example, yellow. The information on the display screen shows, at a glance, how many rooms are filled/empty, who is in each room and who is assigned to each patient.

For each patient, one or more disotypes may be displayed as one visual shield as illustrated in FIG. 1. The patient data may be extracted in real time from the underlying medical information system.

Figure 19:
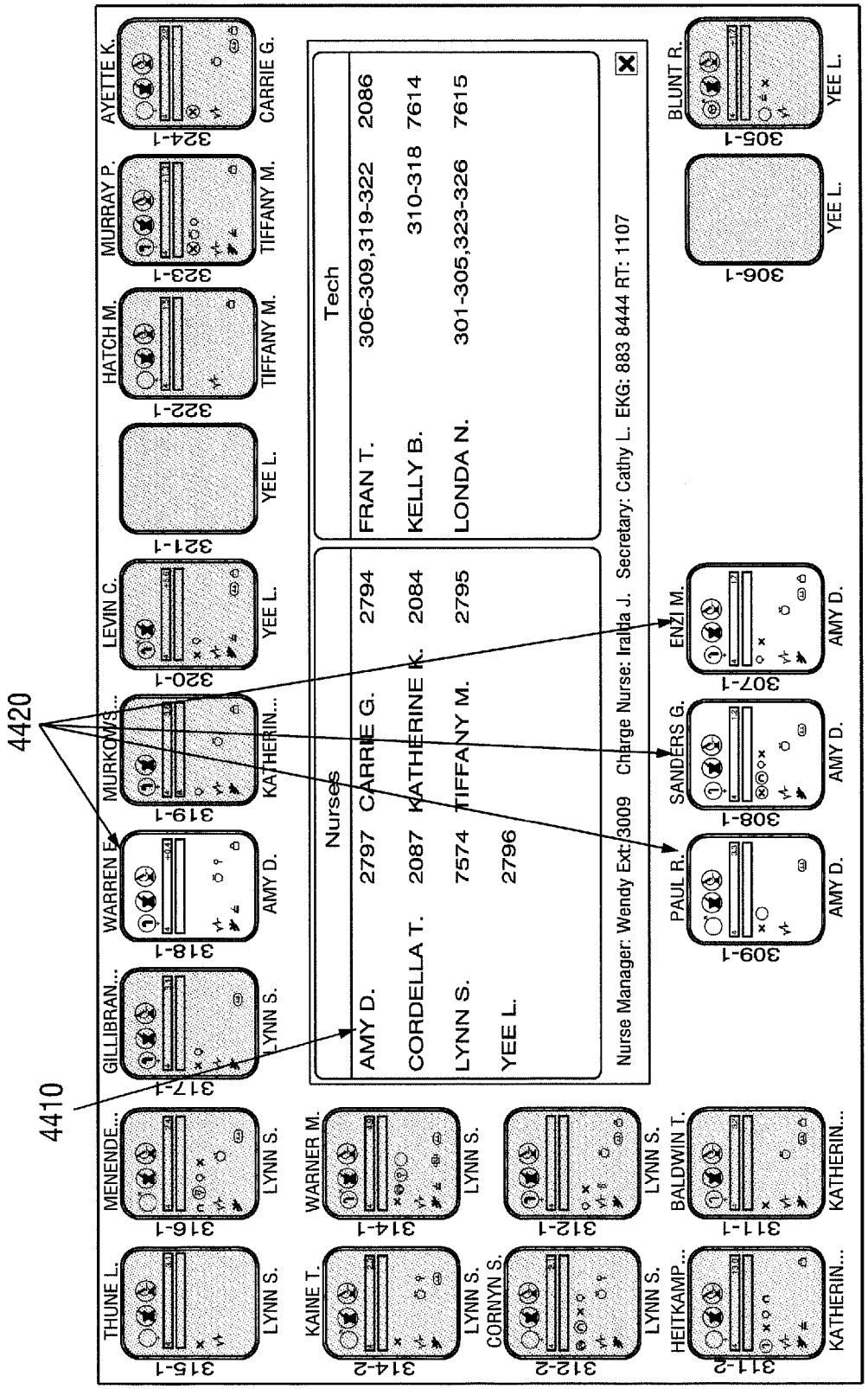
FIG. 19 illustrates an embodiment of a screen shot showing a detail screen that follows filtering by nurse assignment.

In various embodiments the underlying data are available by selecting (e.g., by clicking or touching the disotype which "drills down" to the data) to create a visual navigation to the underlying data. FIG. 19 is a screen shot illustrating detail on nurse selection with patients sorted by nurse assignment. In the illustrated example, the nurse selected is Amy D. 4410 (as shown by the highlight of the nurse's name) and the patients assigned to Amy include the patients in rooms 318-1, 309-1, 308-1 and 307-1. The shields 4420 of the patients assigned to Amy may remain active and those not assigned to Amy may be faded (shown in grayscale in FIG. 19). The selection of a nurse or a technician and the shields corresponding to the selection may be displayed on, for example, a touch screen display. In various embodiments, the screen display remains static until another area of the screen is touched or selected.

Figure 20:
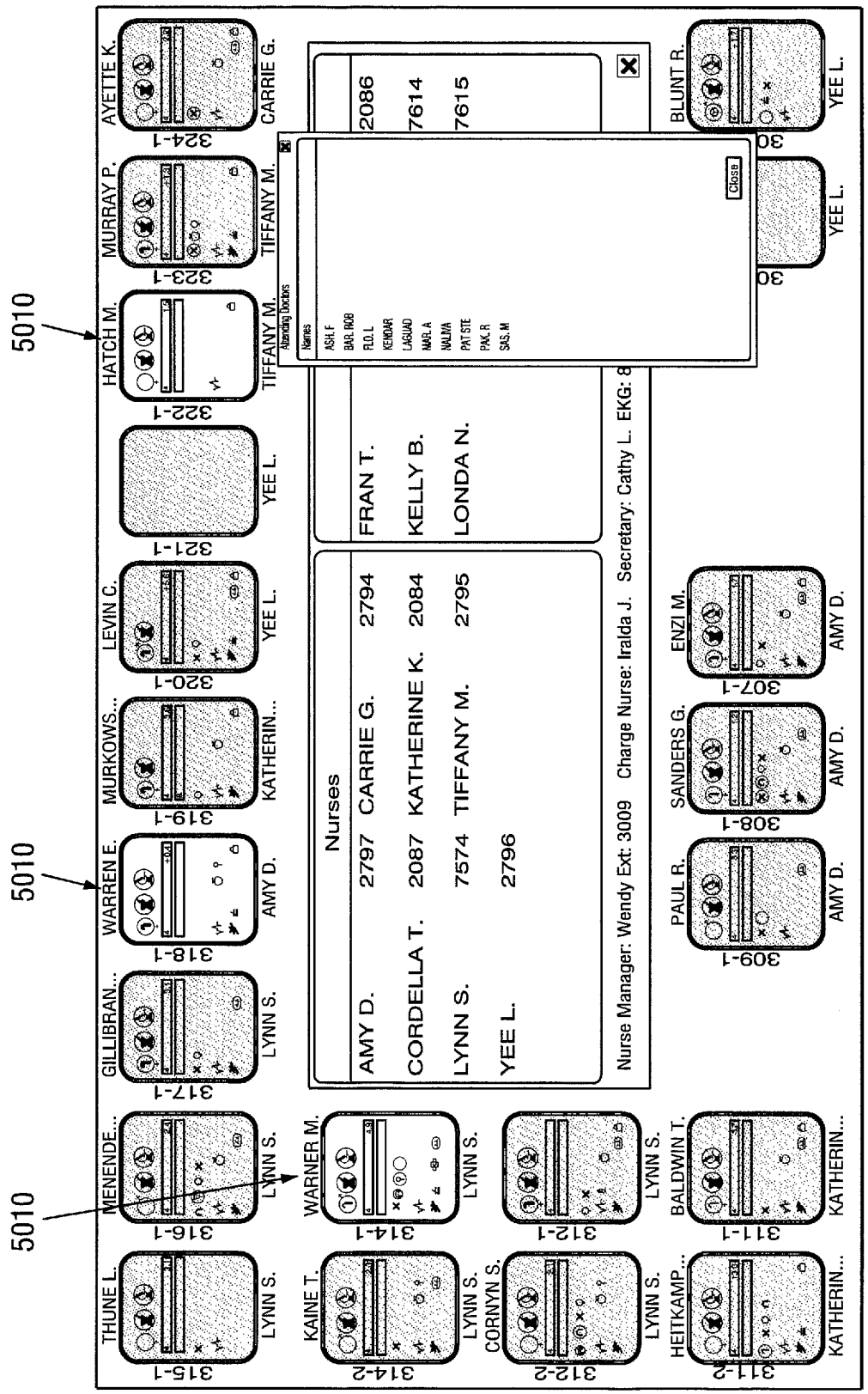
FIG. 20 illustrates an embodiment of a screen shot showing a doctors list presented based on a selection of one doctor.

FIG. 20 is a screen shot illustrating a doctors list for patients in a particular nurse area. As shown, when a doctor's name is selected, the shields 5010 for the patients assigned to that doctor remain prominent and all other patient shields fade to the background. The attending doctors data may be displayed until a "close" icon is selected.

Figure 21:
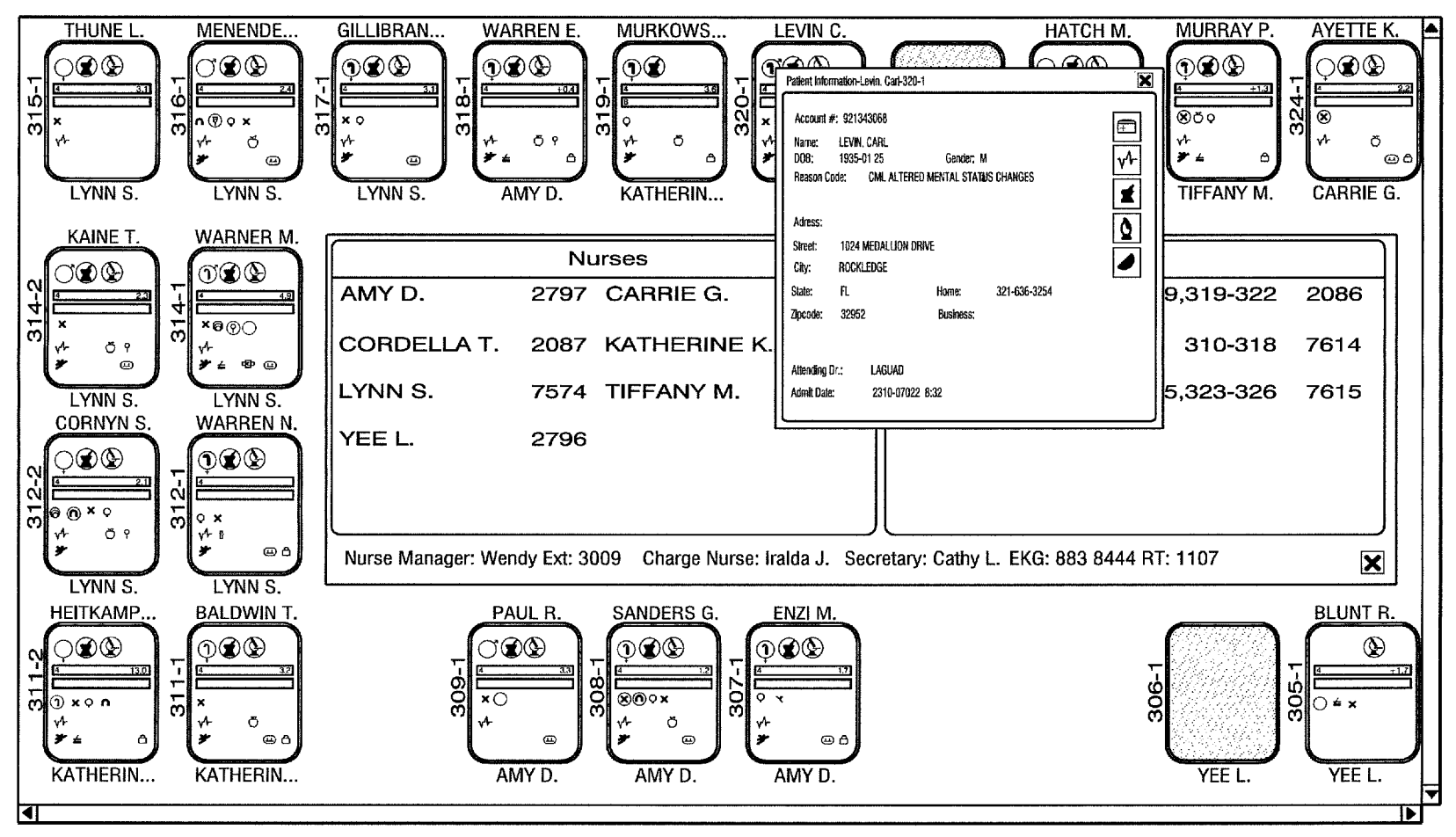

In various embodiments, the display screen may be used to display patient information. FIG. 21 is a screen shot illustrating detail on patient demographic information. In this example, the demographic information for Levin in room 320-1 includes name, address, date of birth, attending physician name, date admitted and a reason code. The reason code displays the reason the patient was admitted to the hospital. The drop down may also show disotypes such as prescriptions and labs that may be selected from the demographic screen. The demographic information may be displayed until the user closes the screen by selecting a "close" icon or an "x."

Figure 22:
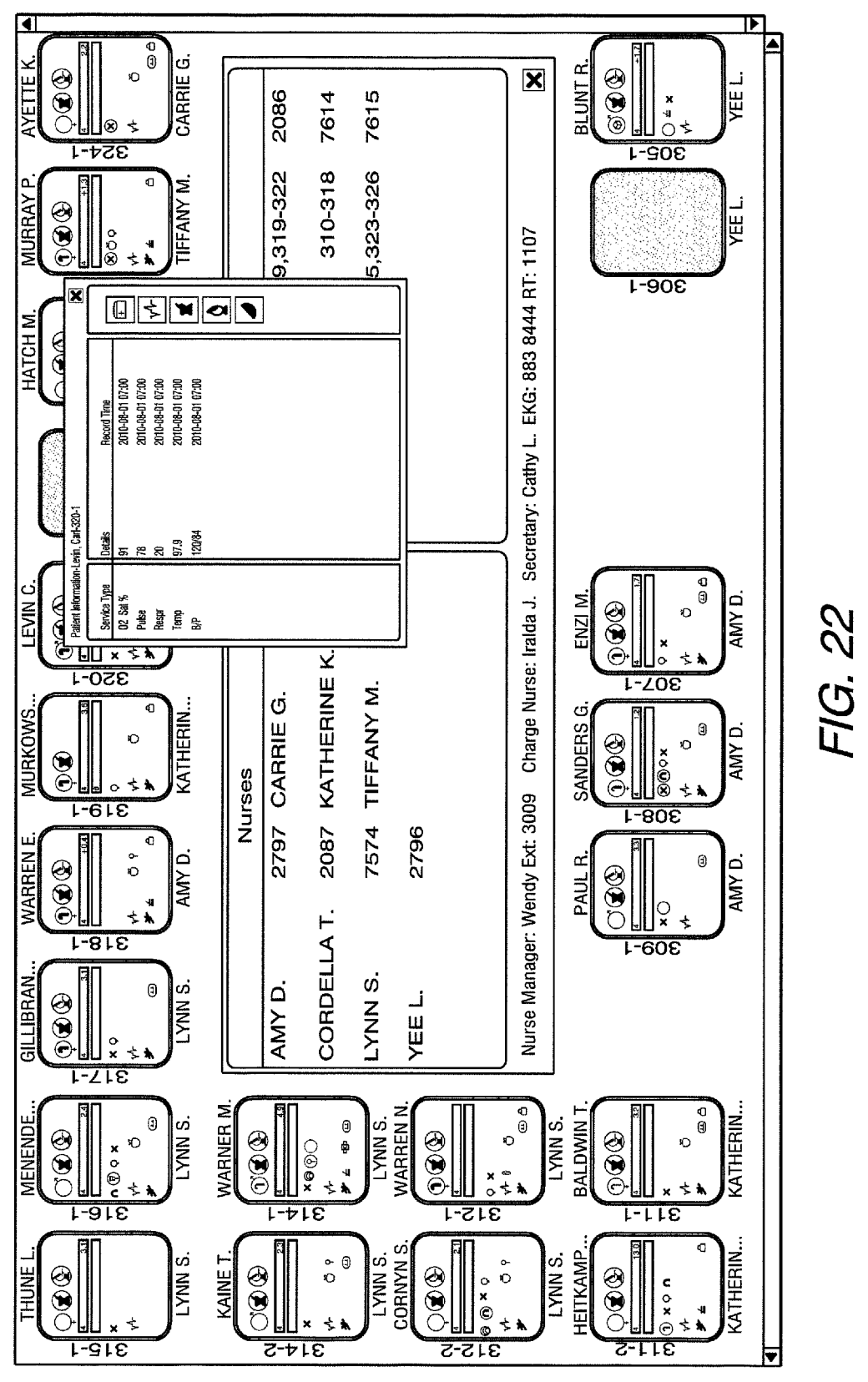

FIG. 22 is a screen shot illustrating detail on vital signs. As in FIG. 21, the drop down display may include patient name and assigned room number. The vital sign information may include a column of vital service types and corresponding columns showing the detail for each service type and the time the detail was recorded. The vital service types may include, but are not limited to, pulse, respiration, temperature, blood pressure, etc. The patient data may be extracted in real time from an underlying medical information system so that large amounts of data may be displayed on, for example, a static or mobile touch screen. This may eliminate the need for a nurse to obtain a patient chart and read the data on the chart, data which may have been handwritten and difficult to read. Because the data are extracted in real time, the data displayed are the most recent data.

Figure 23:
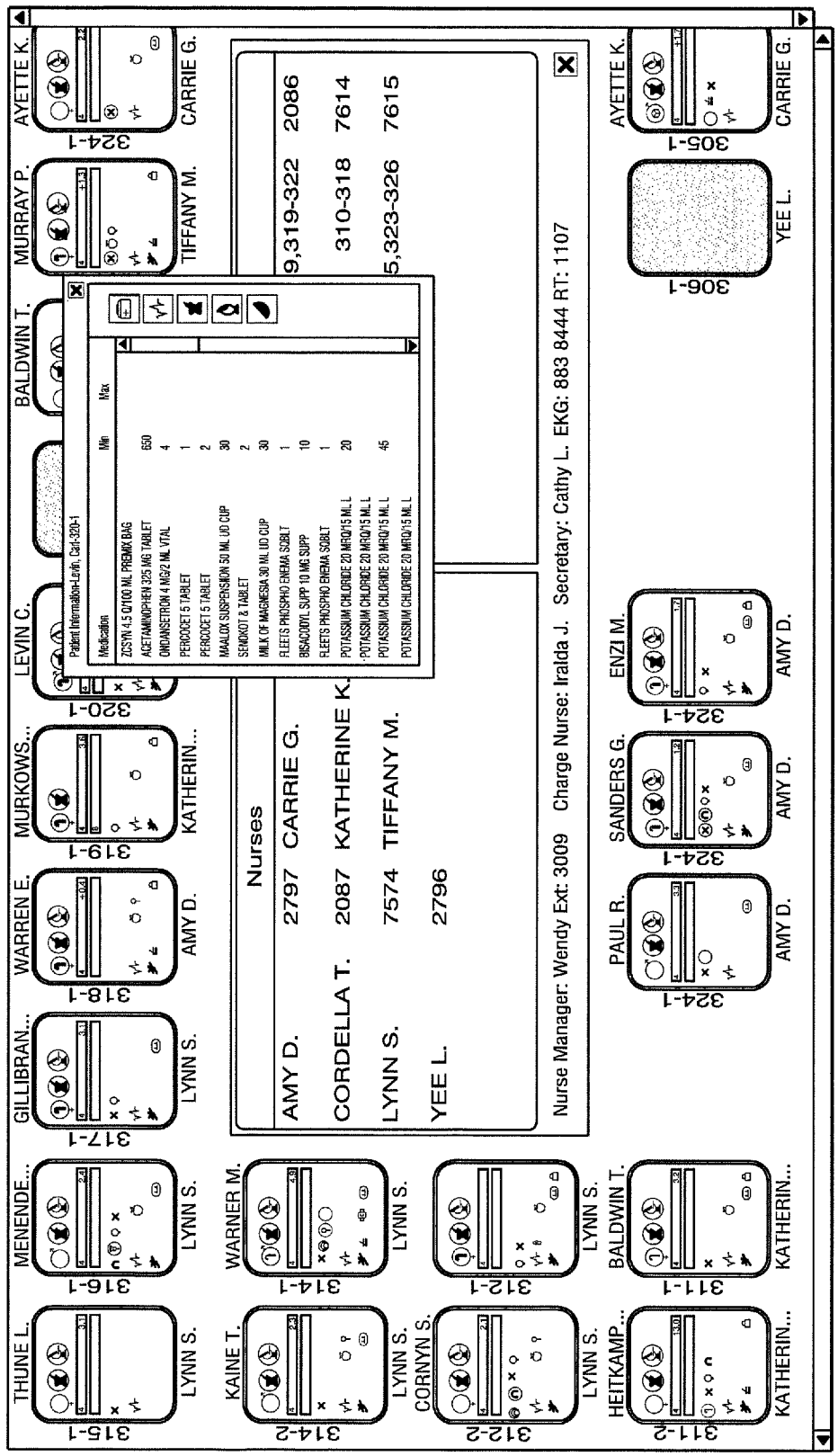
FIG. 23 illustrates an embodiment of a screen shot showing a detail screen of medications.

FIG. 23 is a screen shot illustrating detail on medications that lists the medications prescribed and a minimum and maximum dosage. In the example shown, only a minimum dosage is shown, indicating that the dosage should not be varied.

Figure 24:
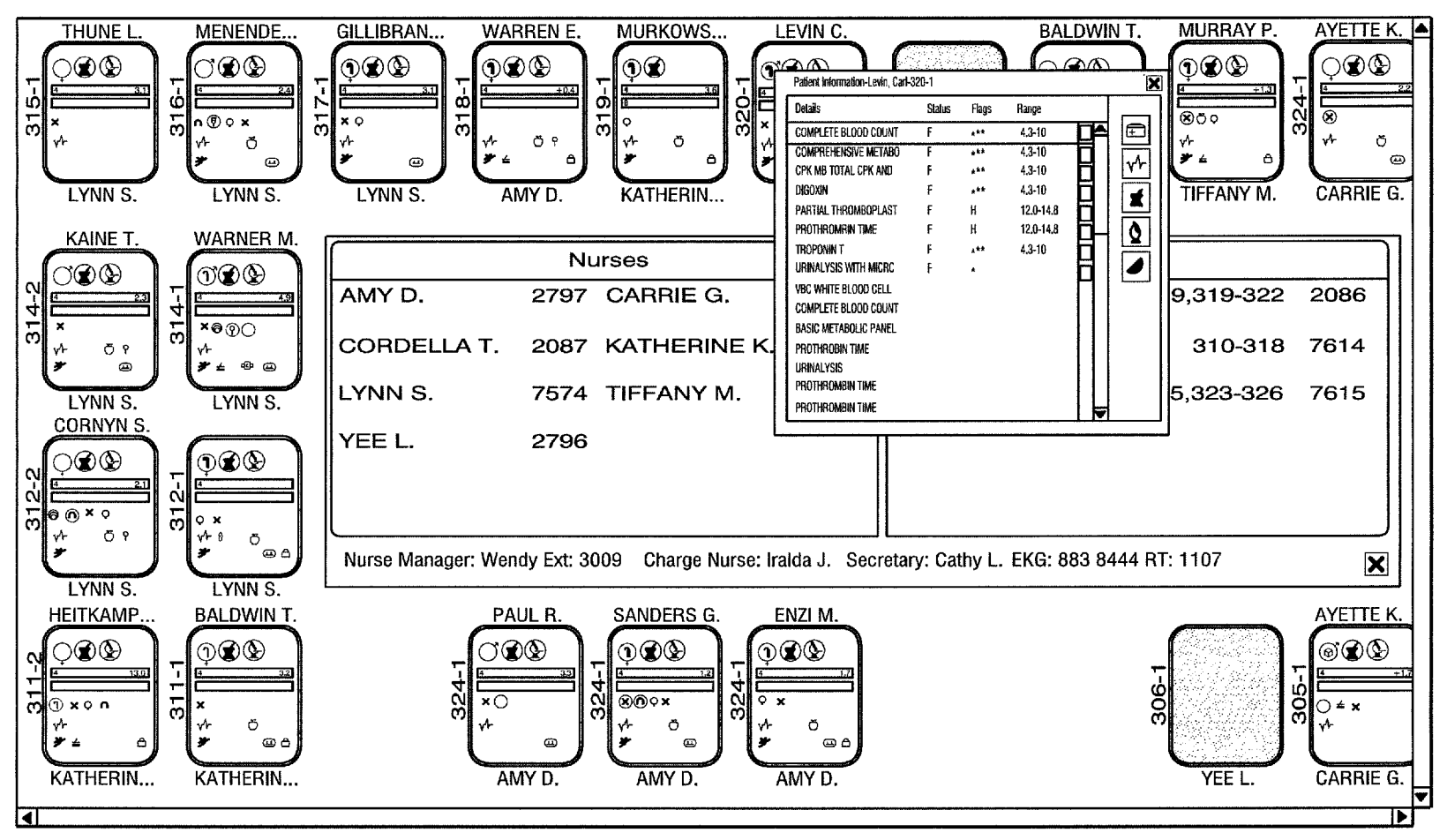
Figure 25:
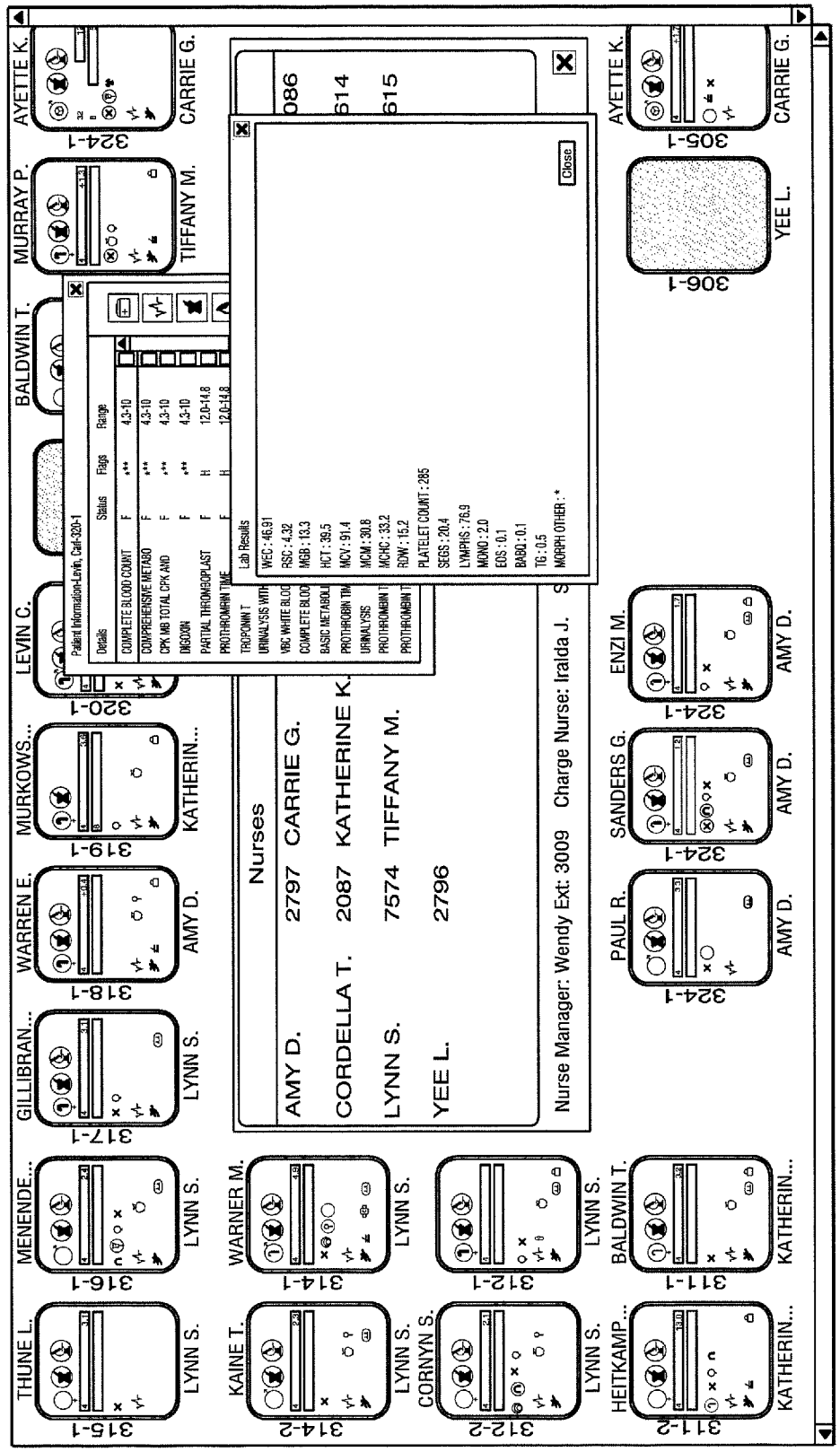
FIG. 25 illustrates an embodiment of a screen shot showing a detail screen of labs with further detail showing lab results.

FIG. 24 is a screen shot illustrating detail on labs and FIG. 25 is a screen shot illustrating a further detail on one lab; a complete blood count in the example shown. As shown in FIG. 24 multiple different labs ordered for the patient are displayed and the user may scroll down to see additional labs in the list. The lab list may include a status column showing the status of the lab, such as F for final, and flags associated with each lab type to alert the user that a lab result is normal or abnormal. Another column may show the normal range for the measurement. From the list of labs ordered, each specific lab that has been filled may have a data available link (right column) that may be selected to show the results of the specific lab as shown in FIG. 25. The lab detail illustrated is a complete blood test, thus the lab results show white blood count, red blood count, etc.

Figure 26:
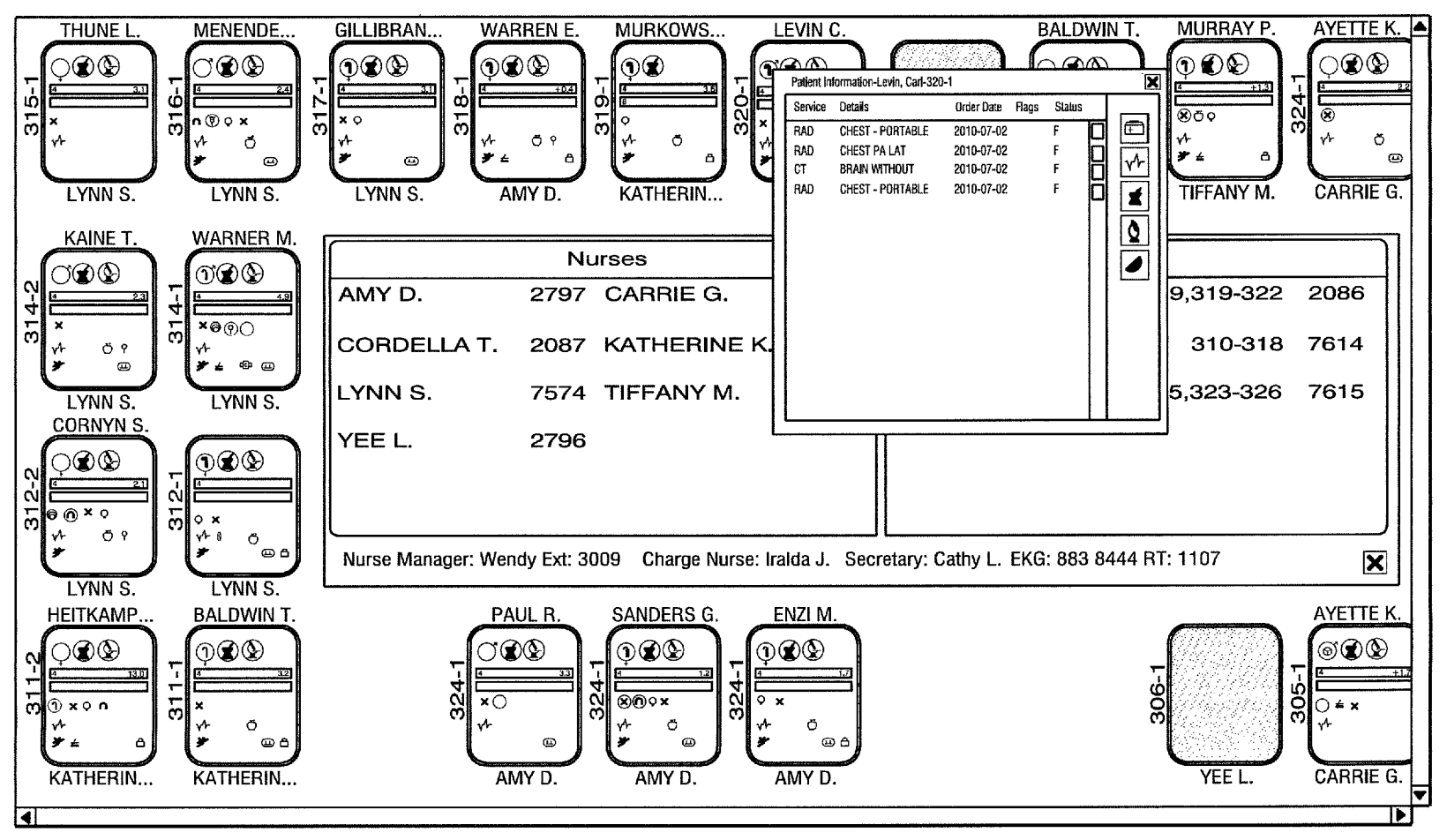
Figure 27:
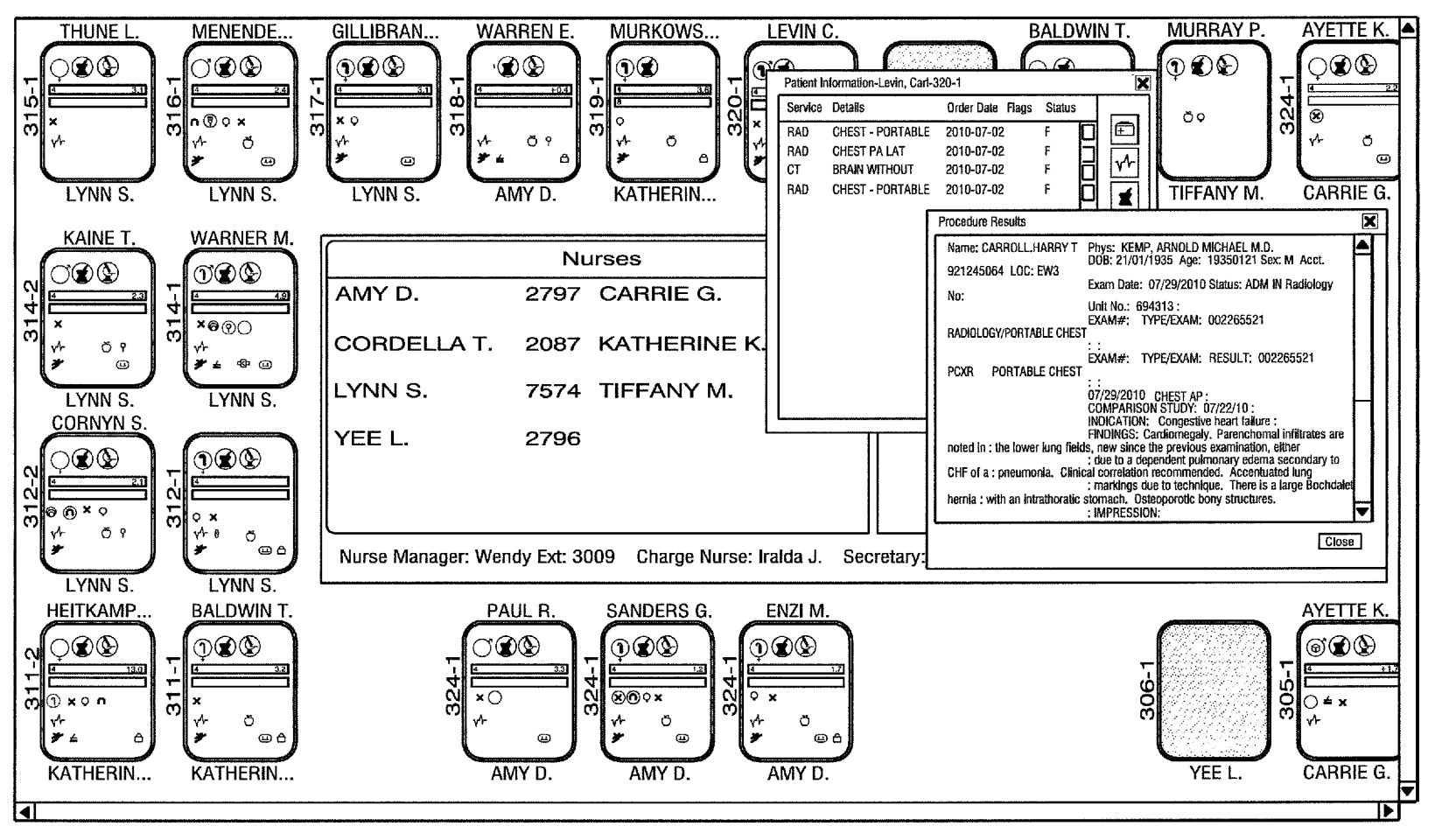

FIG. 26 is a screen shot illustrating detail on procedures showing the procedures ordered for patient Levin in room 320-1. The drop down screen displays the service ordered, details about the service, date the service was ordered, flags associated with the results of the service and status. For example, the first service ordered is radiology and the specific service is a portable chest x-ray, ordered on Jul. 2, 2010 with a status F indicating that the results are final (partial results may be made available before being vetted). The far right column provides access to additional information about the results. FIG. 27 is a screen shot illustrating detail on one procedure report. The drop down screen displays the radiologists noted results of the chest x-ray from FIG. 26.

FIGS. 19 through 27 show examples of detail screens, although one skilled in the art should realize that the particularities in the information displayed should not be construed as limiting. Various display configurations and corresponding drop down screens may be chosen and optimized for a particular application to achieve a desired patient information display.

In various embodiments, patient information may be sorted and/or filtered for, for example, caregiver workflow or to focus on specific elements of the information, such as LOS, diagnostic code, lab results, etc. For doctors, their patients may be scattered all over a hospital campus, in which case some type of grid display may be a more effective way for them to understand the status of all of their patients at a glance. As shown in the embodiment illustrated in FIG. 28, the patient shields are not displayed according to the floor plan but rather each patient shield is positioned next to the previous one on the screen, aligned in rows and columns.

In various embodiments, the patient shields are not initially displayed in any specific order. The patient shields may be sorted based on patient name, diagnostic code, assigned doctor, type of labs on order, etc. Thus, sorting and filtering may be performed on any piece of information associated with the patient shield. The sort criteria may be textual information such as patient name, assigned doctor, DRG code, etc., or visual information, such as labs on order, procedures on order, length of stay (LOS), etc.

Figure 28:
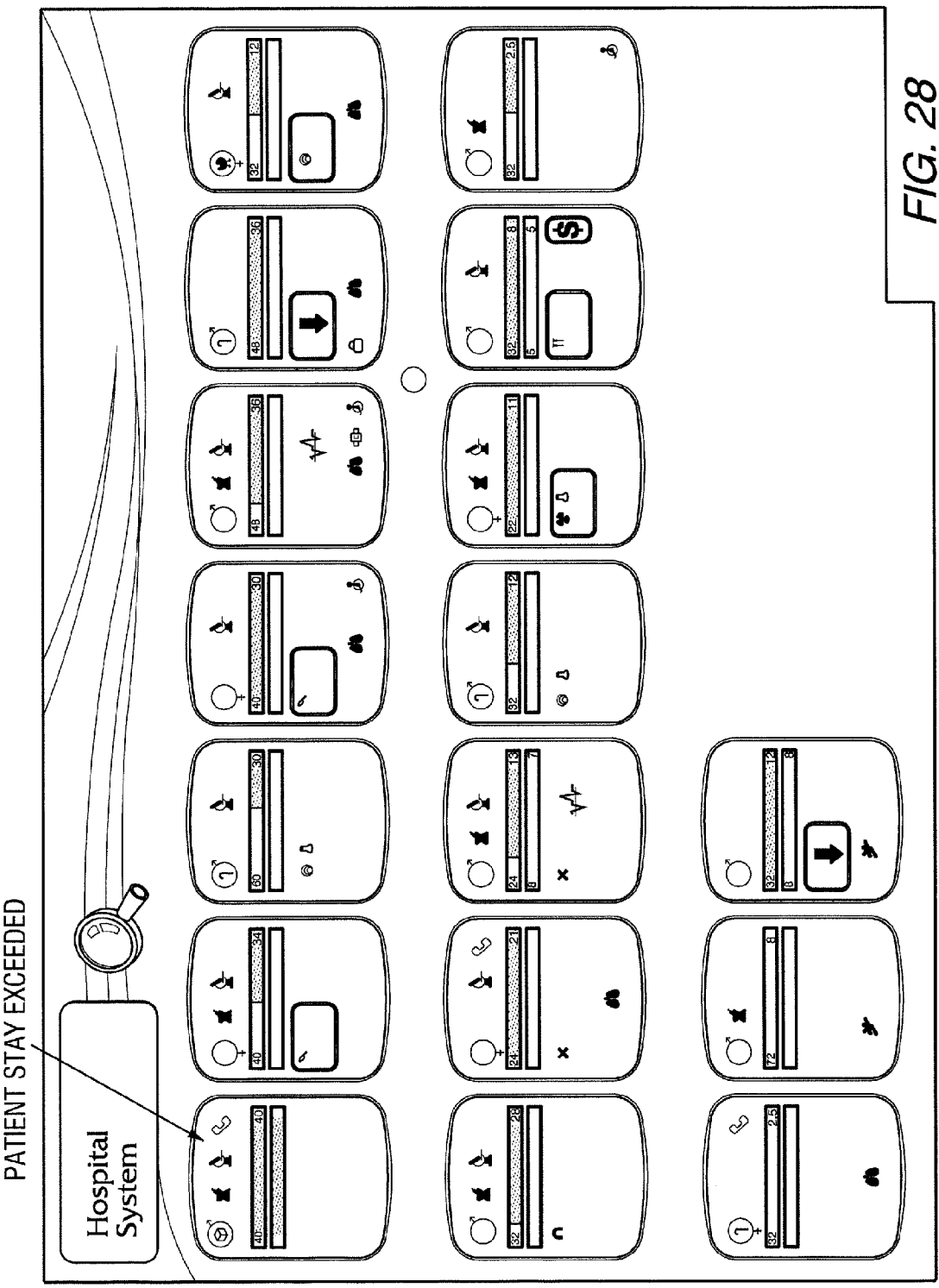
FIG. 28 illustrates an embodiment of a screen shot showing patient shields displayed for viewing.

In the embodiment illustrated in FIG. 28, patients may be viewed regardless of their location within a facility. The shields may include a title field below the patient shield, which may be populated with the patient's name or may be populated with other information such as building/room numbers, patient codes, diagnostic codes, etc., which may be definable by the user.

Figure 29:
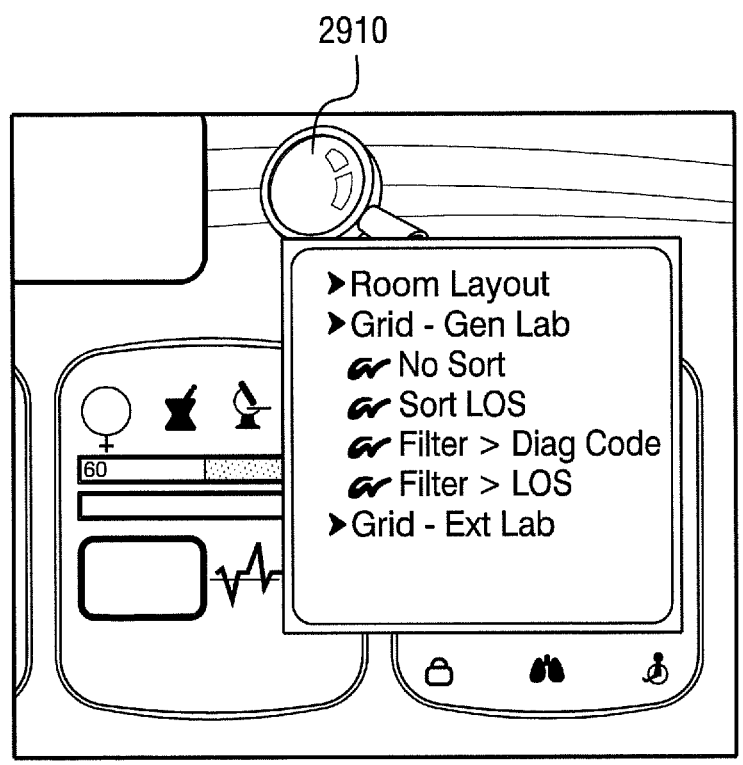
FIG. 29 illustrates an embodiment of a screen shot showing an example of sort and/or filter criteria.

As shown in FIG. 29, a user may sort the patient shields according to any information associated with the patient shields. For example, the user may sort based on time remaining in the length of stay LOS field. As shown, a magnifying glass icon 2910 when selected may show a drop-down list of sort and filter criteria, and the user may select the sort/filter of choice. The sort and filter menu illustrated in FIG. 29 is for illustration only and should not be construed as a limitation of the sort and filter criteria that may be available for selection. The result of the sort is shown in FIG. 30, where the Charts are sorted and displayed based on the LOS time remaining.

Figure 30:
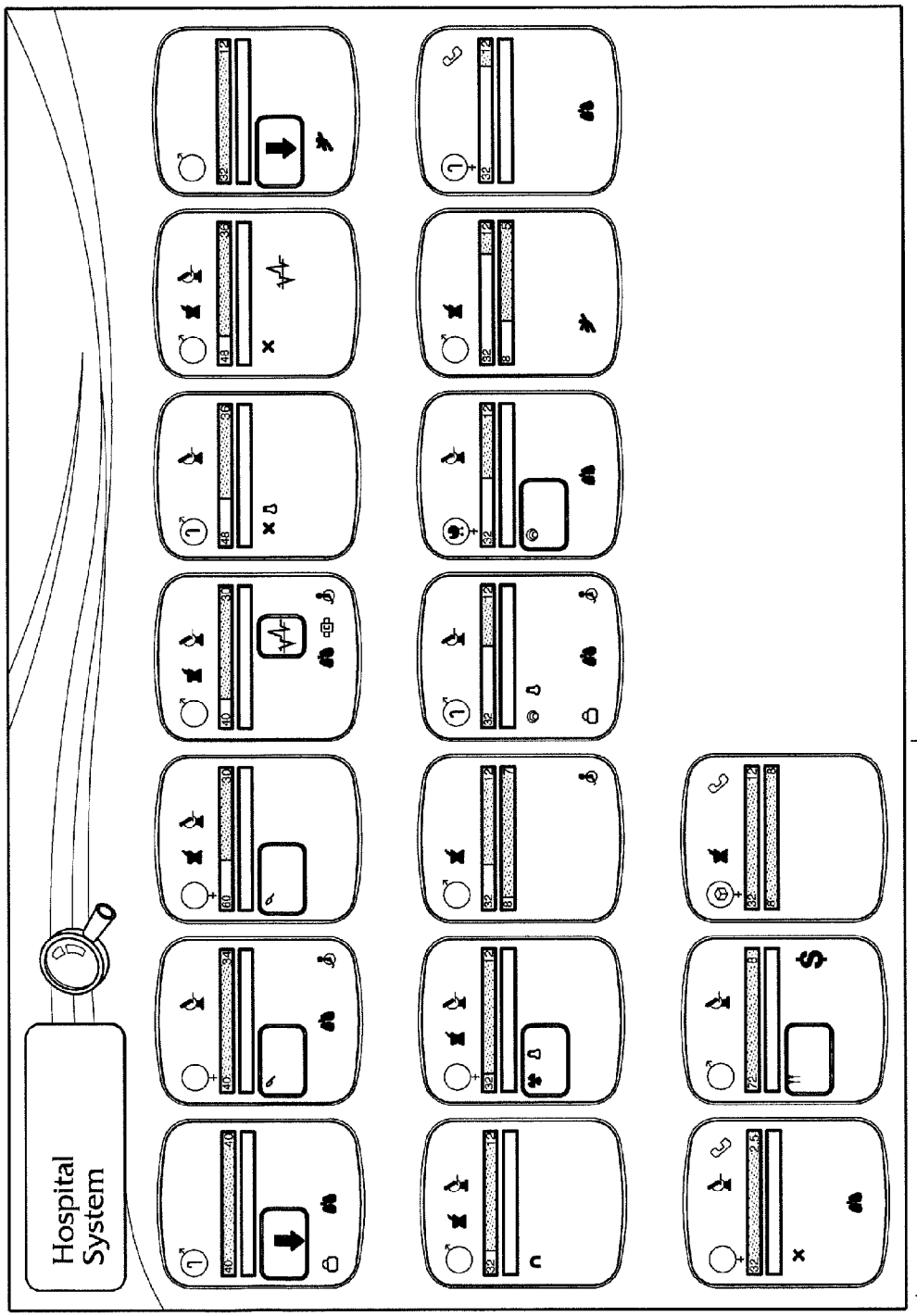
FIG. 30 illustrates an embodiment of a screen shot showing the patient shields of FIG. 28 sorted by length of stay.
Figure 31:
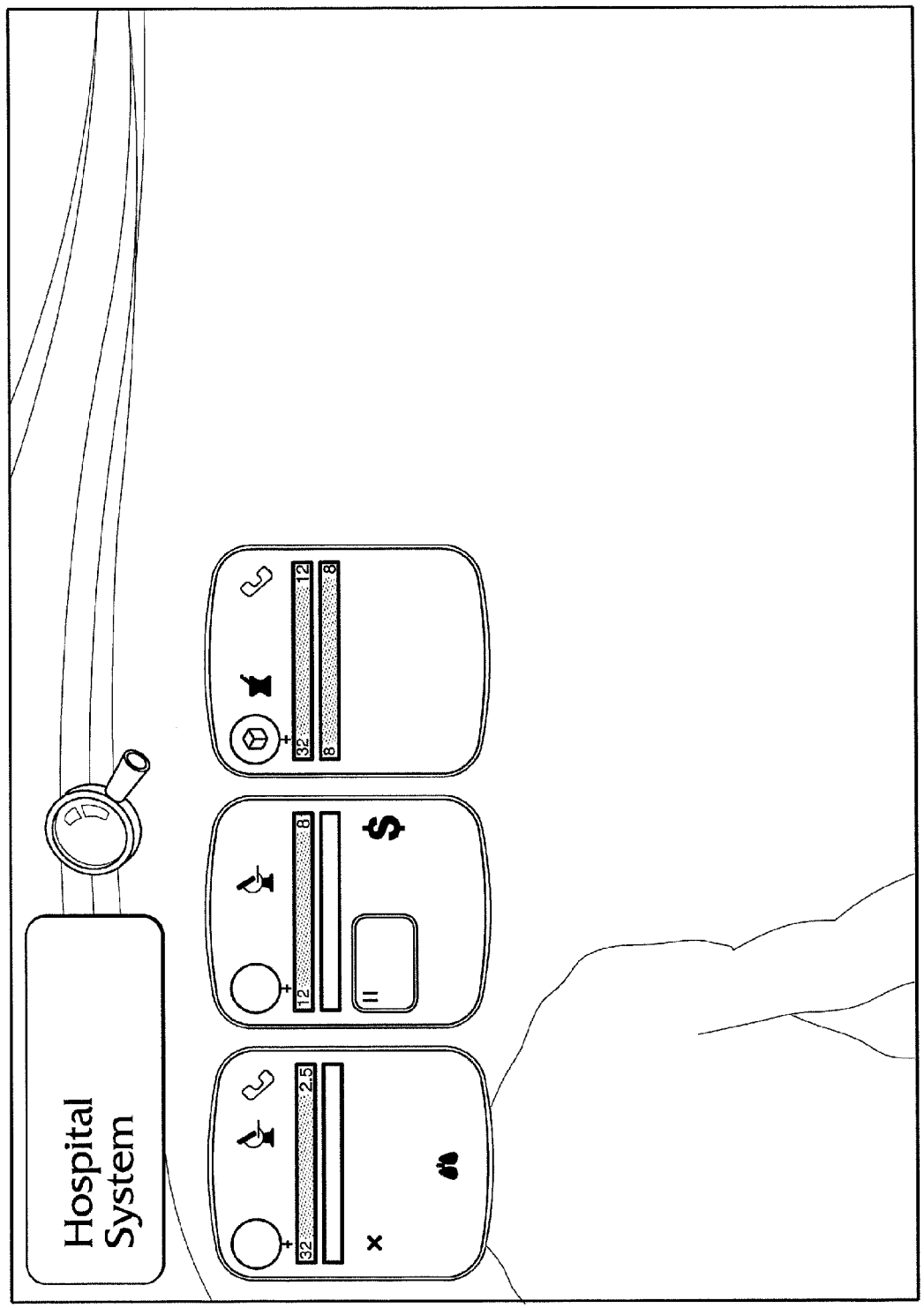
FIG. 31 illustrates an embodiment of a screen shot showing the sorted shields of FIG. 30 filtered by exceeding length of stay.

In FIG. 30 the patients that have exceeded the Average Length of Stay (ALOS) for their diagnostic code are shown at 3010. The user may choose to filter to the patients that have exceeded their ALOS by selecting the appropriate item from the filter menu, for example selecting Filter>LOS. In FIG. 31, the patient shields are filtered to the patients whose ALOS has been exceeded. Sorting helps all types of users and caregivers to monitor and respond to different types of situations at a glance for, for example, case management intercession.

Figure 32:
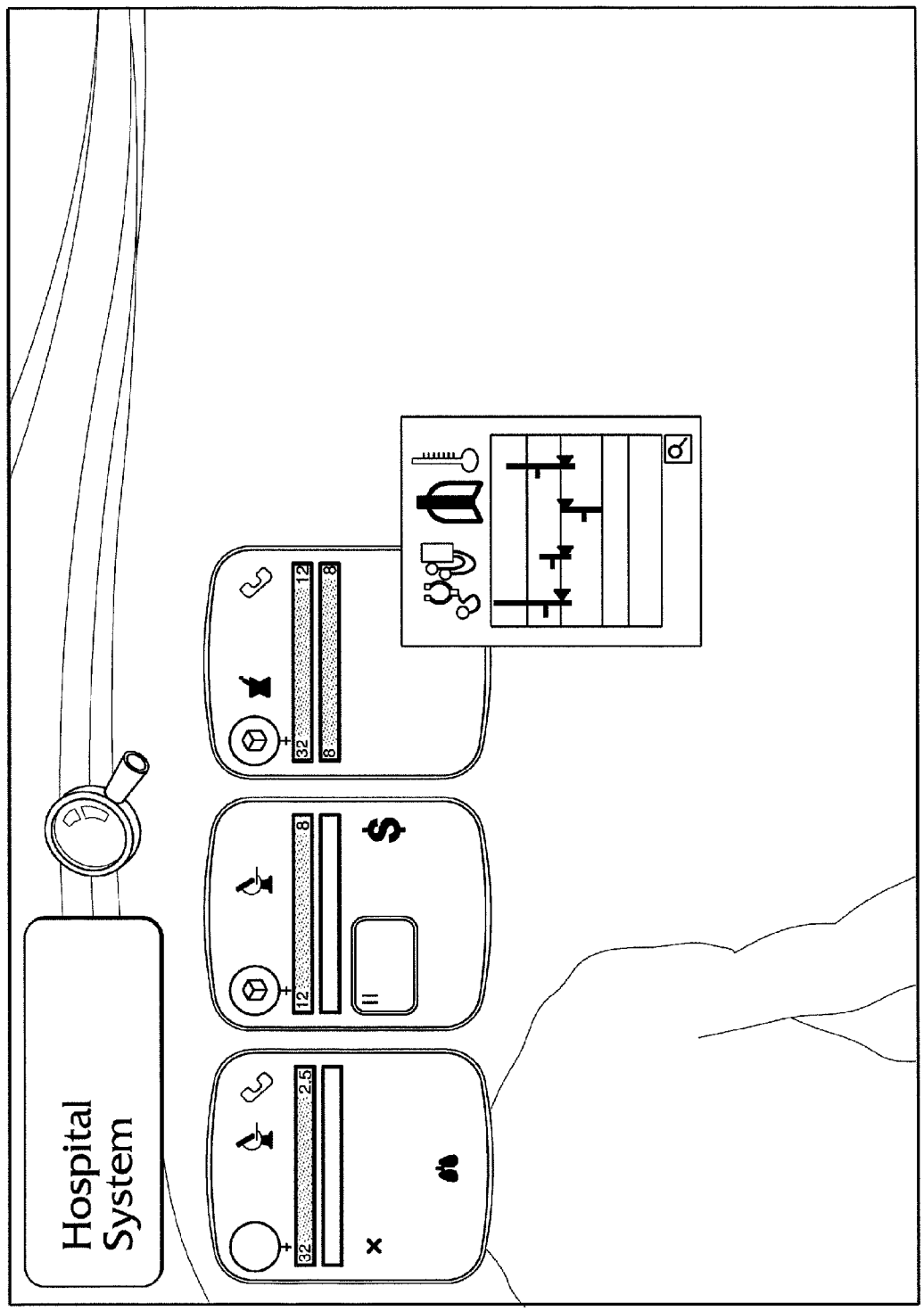
FIG. 32 illustrates an embodiment of a screen shot showing a vitals table for a specific patient.

According to an embodiment, detail or "drill down" navigation may be available. In the example shown in FIG. 32, the user may select a vitals table for a specific patient, which shows the highest, lowest, average, and current reading for each of pulse, blood pressure, respiration rate, and temperature.

Embodiments provide many benefits to the viewer. For example, users such as a caregiver and/or physician may focus on only their patients, because only those patients that are assigned to that person may be displayed. The user may then filter or sort those patients displayed based on, for example, diagnostic codes, LOS, etc. to provide comparative associations between patients with similar attributes based on the sort and/or filter. For example, a user may filter out all but pneumonia patients, view the vitals and labs, and based on that determine the priority and aggressiveness of the treatment programs for each of those patients—noting which patients are in a worse condition than the others and focus on them first.

Figure 33:
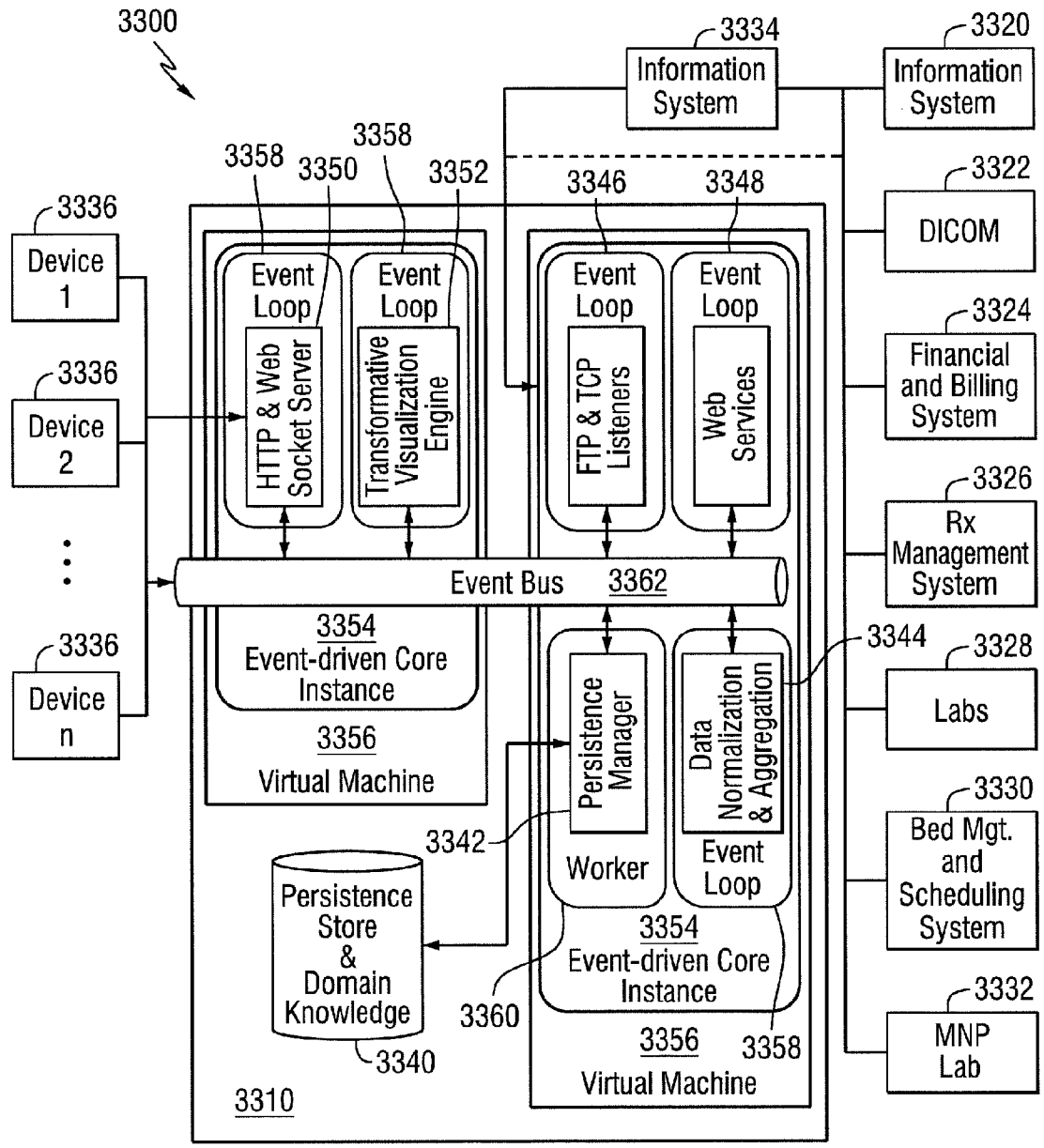
FIG. 33 illustrates an embodiment of a system in which the processes of embodiments of the present invention may be used.

Using the methods and systems of the present invention, a user such as a physician may examine multiple campuses to determine, based on DRG and treatment results, if a specific area of the hospital is having more success for a specific DRG than others, and the user may drill down capabilities to determine what treatment options were different, if any. An embodiment of a system 3300 in which the processes of embodiments of the present invention may be used is illustrated in FIG. 33. As illustrated in FIG. 33, a visual language engine (VLE) 3310 may include virtual machines (e.g., Java virtual machines) 3356 that host event-driven core (EDC) instances 3354. The EDC instances 3354 may perform two functions: core services and the functions of modules 3342, 3344, 3346, 3348, 3350 and 3352. EDC services are services that may be directly called from a module 3342, 3344, 3346, 3348, 3350 and 3352 and may include clients and servers for transmission control protocol/secure socket layer (TCP/SSL), hypertext transfer protocol (HTTP), and web sockets; services to access an event bus 3362; timers, buffers, flow control, file system access, shared maps and sets, logging, access configuration, servers (e.g., Sockjs-node), and deploying and undeploying EDC instances 3354. Various of the other functionality of the system 3300 may be provided by the modules 3342, 3344, 3346, 3348, 3350 and 3352. The EDC instances 3354 may contain two subsystems—a worker subsystem 3360 and an event loop subsystem 3358. The subsystems 3358, 3360 may host the various modules within the system 3300. The event loop subsystems 3358 may create a thread to execute non-blocking modules (i.e., modules that do not block other modules from executing). In various cases a module may need to do something either computationally expensive, or that might block, such as connecting to a database (e.g., as may be the case of a persistence manager module 3342 in the system 3300 which reads and writes to a persistence store 3340). In such a case, the worker subsystem 3360 may be created and executed by a background thread pool.

Various modules may be utilized within the VLE 3310, including the persistence manager module 3342, a data normalization & aggregation module 3344, an FTP & TCP listener module 3346, a web services module 3348, an HTTP & web socket server module 3350, and a transformative visualization engine module 3352. The modules 3342, 3344, 3346, 3348, 3350 and 3352 may interact through the event bus 3362 to deliver functionality to transform data from medical systems 3320, 3322, 3324, 3326, 3328, 3330 and 3332 into a visual language for display on various output display devices 3336.

The VLE 3310 may be implemented on any type of computing device, such as, for example, a server. The persistence store 3340 may be any type of volatile or non-volatile memory, such as a cache memory. Domain specific knowledge held within the persistence store 3340 may be used by the VLE 3310 as described hereinbelow. The VLE 3310 may be in communication with various systems, including one or more information systems 3320, 3334 such as, for example, electronic medical records systems, hospital information systems, electronic health record systems, etc. The VLE 3310 may also be in communication with one or more imaging systems 3322 such as, for example, digital imaging and communication in medicine (DICOM) systems, picture archiving systems, etc. The VLE 3310 may also be in communication with one or more financial and billing systems 3324, one or more prescription management systems 3326, and one or more laboratory systems 3328. The VLE 3310 may also be in communication with one or more hospital systems 3330 such as, for example, bed management systems, scheduling systems, single sign on (SSO) systems, communication/messaging systems, etc. The VLE 3310 may also be in communication with one or more molecular, nuclear and pathology lab systems 3332.

The systems 3320, 3322, 3324, 3326, 3328, 3330 and 3332 may be in communication with the VLE 3310 via any type of network that uses, for example, health level 7 (HL7), an application programming interface (API), file transfer protocol (FTP), transmission control protocol/internet protocol (TCP/IP), etc. The systems 3320, 3322, 3324, 3326, 3328, 3330 and 3332 may be in communication with the VLE 3310 via one or more information systems 3334 such as, for example, electronic medical records systems, hospital information systems, electronic health record systems, etc.

The VLE 3310 may be in communication with devices 3336, which may display the medical dialect of the visual language as described in connection with various embodiments herein. The devices 3336 may be any type of device that is capable of displaying such visual language such as, for example, handheld devices such as smartphones and tablet computers; wearable devices such as smart watches and glasses-type devices; fixed displays such as desktop workstations and wall mounted monitors; displays that are integral with equipment such as x-ray machines; portable devices such as mobile workstations; and holographic and head-up display devices.

The VLE 3310 may utilize the modules 3342, 3344, 3346, 3348, 3350 and 3352 to convert raw, atomic data (i.e., the lowest level of detail about a patient, system, or piece of equipment that provides the base data for data transformations and aggregations within the system 3300) from the various medical systems 3320, 3322, 3324, 3326, 3328, 3330 and 3332 into the visual language described herein in connection with various embodiments. Each system 3320, 3322, 3324, 3326, 3328, 3330 and 3332 may produce atomic data that, by itself, cannot be transformed into the visual language and therefore it may be desirable to normalize and aggregate the data into the persistence store 3340 for further processing. Intake services modules such as an FTP & TCP listeners module 3346, the web services module 3348, and the HTTP & web socket server module 3350 (pathway not shown in drawing) may "listen" for changes on the network. The atomic data may also be received, in various embodiments, via a web/rest service call-out module (not shown) that may use API calls to a centralized information system such as the persistence manager 3334 to retrieve atomic data. Such an embodiment may also allow for the retrieval of semi and fully aggregated data that was normalized and aggregated within, for example, the persistence manager 3334.

In various embodiments, as data are received by the intake modules 3346, 3348 and 3350, the data may be pushed onto the event bus 3362 so that processing modules that are "listening" on the event bus 3362 may receive the data for further processing. In such an embodiment, the data that was pushed to the bus 3362 by the intake service modules 3346, 3348 and 3350 are retrieved by the data normalization and aggregation module 3344. The module 3344 may use the domain knowledge 3340 to determine how the atomic data need to be normalized, and then aggregated into a form that fuses the atomic data into aggregate data elements based on the domain knowledge 3340, and sent back to the event bus 3362 for further processing. Normalization rules may include ensuring that the units of the atomic data are the same, that any identification of the specific data elements is mapped to a common identifier (based on rules from the domain knowledge 3340 that define the mapping from the atomic data to the larger data structures) that may be utilized to fuse the atomic data into an aggregate data record that may be transformed into the visual language. As the data normalization & aggregation module 3344 processes the data events it receives, it may make service calls via the event bus 3362 to the persistence manager module 3342, which may retrieve any normalization and aggregation rules from the domain knowledge 3340, as well as any other units of information that may have already been processed by the data normalization & aggregation module 3344 so that a higher level of fusion may continue with the construction of the aggregate data record. Once finished with the retrieval of the domain knowledge 3340 and any partial or whole aggregate data records, the current atomic data may be fused with the aggregate data record by the data normalization & aggregation module 3344 and pushed back onto the event bus 3362 for the persistence manager module 3342 to process and persist into the persistence store 3340. Such processing may continue every time new atomic data are sent in via the medical systems 3320, 3322, 3324, 3326, 3328, 3330 and 3332. Each time an aggregate data record is updated and placed on the event bus 3362, other modules may listen for that event to do further processing. One embodiment includes validation modules that semantically check the aggregation to ensure the validity of the data. Another embodiment may include validation modules that perform lookups into other database systems to fill in missing information driven by keys within the data, mapped via the domain knowledge 3340 the systems 3320, 3322, 3324, 3326, 3328, 3330 and 3332 for lookups. For example, the RX management system 3326 may only send out a code for a specific medicine type, and the validation module may use the code to look up the full name of the medicine from a drug database, and validate semantic elements of the aggregate data record to prevent errors in the prescription order process so that the medicine ordered correlates with a specific DRG code, and if not a flag may be set in the aggregate data record, which may be used by the visual language to add a morpheme to be visualized as a warning indication within a disotype. It can be understood that various validation techniques may be utilized to validate the accuracy and integrity of the data moving through the system.

In various embodiments, each time the data normalization & aggregation module 3344 updates an aggregate data record and places it on the event bus 3362, the transformative visualization engine 3352, which may also be subscribed to such types of events, may retrieve the aggregate data record from the event bus 3362 and either use an API call via the event bus 3362 to access the persistence manager module 3342 to retrieve the domain knowledge about the visual language dialect as well as other information surrounding the aggregate data record so that it can then apply the grammar rules, along with the morphology and the syntax of the visual language, to create the visual language elements that will be formulated and sent to the display devices 3336.

It should be noted that in various embodiments subject matter experts are utilized in creating a specific visual language dialect, which is then translated into the domain knowledge, which may then be utilized by the transformative visualization engine (TVE) 3352 to map the aggregate data records to the visual language. The TVE 3352 may use three levels of the language construction—words (disotypes), which are put together to create sentences (a shield, or graphic layout), and to tell a story (provide situational awareness) by combining multiple sentences together to form a display with multiple shields, with each shield containing multiple disotypes, and each disotype made up of various affixes to express the multidimensional data within a single disotype. As described herein in connection with various embodiments, the disotypes may be formed by a set of descriptive rules and visual vectors that represent both the root concept (the stem), and the vectors that make up the various affixes that add meaning about various states, statuses, and/or conditions of that root concept. This may be matched with a set of rules that define how the aggregate data record is mapped to the root concept as well as the affixes that convey the extra semantic meaning of the supporting root concept affixes. This may be stored within the domain knowledge 3340 so that the TVE 3352 may apply polyglot transformations on the aggregate data record to generate the appropriate disotype with the stem and appropriate affixes expressed correctly within the visual language. The disotype may be pushed to the event bus 3362 so that the display devices 3336 may then transfer the vector information to the localized displays and render them. The persistence manager module 3342 may also persist the disotype raw vector form so that display devices 3336 that do not have a "push" capability to receive the data directly may utilize other retrieval mechanisms such as, for example, via HTTP calls to the HTTP & web socket server module 3350, direct access to the event bus 3362, or through web service calls to the web service module 3348. Data may be pulled or pushed to the display devices 3336 depending on the specifics of the visualization capabilities of that device. It can be understood that other delivery methods, such as hybrid delivery methods, may be used to transfer the visual language vector information to the display devices 3336.

Embodiments of the invention may be used with or incorporated in a computer system that may be a standalone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

In another aspect, the invention may be implemented as a non-transitory computer readable medium containing software for causing a computer or computer system to perform the method described above. The software can include various modules that are used to enable a processor and a user interface to perform the methods described herein.

Although embodiments have been described herein in the healthcare environment, it can be understood that embodiments of the invention may be used to display and manage information in the transportation, mining, energy, human and social services, construction, health insurance, project performance, financial, cargo tracking and dispatch, aircraft maintenance, student performance monitoring, supply chain management, shipping, industrial equipment, call center management, vehicle sales, law enforcement, and information technology fields.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

Embodiments of the invention may be used with or incorporated in a computer system that may be a standalone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

In another aspect, the invention may be implemented as a non-transitory computer readable medium containing software for causing a computer or computer system to perform the method described above. The software can include various modules that are used to enable a processor and a user interface to perform the methods described herein.

Although embodiments have been described herein in the healthcare environment, it can be understood that embodiments of the invention may be used to display and manage information in the transportation, mining, energy, human and social services, construction, health insurance, project performance, financial, cargo tracking and dispatch, aircraft maintenance, student performance monitoring, supply chain management, shipping, industrial equipment, call center management, vehicle sales, law enforcement, and information technology fields.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A computer implemented method of displaying a virtual patient chart, the method comprising:
   receiving data relating to a patient;
   generating, using a processor, a graphic representing at least a portion of the received patient data, wherein the generating comprises:
   (a) using a plurality of consistent visual modification rules that convey additional information to the graphic;
   (b) rendering the graphic as a dynamic isotype or disotype representing a base metric associated with the patient data, wherein rendering the disotype further comprises:
      (i) rendering the disotype with multiple dimensions of data wherein multiple attributes are associated with the base metric, wherein each attribute represents a separate dimension of data associated with the same base metric and each attribute is associated with a visual representation which is displayable in association with rendering the disotype, and,
      (ii) dynamically modifying a visual appearance of the disotype in response to comparison of a numerical value associated with the common metric to a threshold value associated with the base metric, wherein modifying the visual appearance of the disotype comprises modifying at least one of a color or a shape of the disotype; and (c) maintaining consistency of semantic meaning of at least one visual appearance of at least one of the attributes associated with the rendered disotype, including retaining the semantic meaning of the visual appearance as applied among different disotypes; and displaying the graphic on a virtual patient chart.

2. The method of claim 1, wherein the rendered disotype includes a representation of status of the patient.

3. The method of claim 1, wherein the visual modification rules include rules that specify displaying color to the graphic when the attribute is of a certain class or value.

4. The method of claim 1, further comprising generating, using the processor, a second graphic representing at least a portion of the received patient data, wherein the generating of the second graphic comprises:
  (a) using a plurality of consistent visual modification rules that convey additional information to the second graphic;
  (b) rendering the second graphic as a dynamic isotype or disotype representing a base metric associated with the patient data, wherein rendering the disotype further comprises:
    (i) rendering the disotype with multiple dimensions of data wherein multiple attributes are associated with the base metric, wherein each attribute represents a separate dimension of data associated with the same base metric and each attribute is associated with a visual representation which is displayable in association with rendering the disotype, and,
    (ii) dynamically modifying a visual appearance of the disotype in response to comparison of a numerical value associated with the common metric to a threshold value associated with the base metric, wherein modifying the visual appearance of the disotype comprises modifying at least one of a color or a shape of the disotype; and
  (c) maintaining consistency of semantic meaning of at least one visual appearance of at least one of the attributes associated with the rendered disotype of the second graphic, including retaining the semantic meaning of the visual appearance as applied among different disotypes.

5. The method of claim 4, further comprising organizing the graphic and the second graphic to increase cognitive recognition by a user.

6. The method of claim 1, further comprising displaying a set of data upon selection of the graphic by a user.

7. The method of claim 4, further comprising enabling a user to sort the graphic and the second graphic.

8. The method of claim 4, further comprising enabling a user to filter the graphic and the second graphic.

9. The method of claim 1, further comprising receiving data relating to at least one piece of medical equipment.

10. A system, comprising:
  a database; and
  a visual language engine in communication with the database, the visual language engine configured to:
    receive data relating to a patient from a medical system,
    generate a graphic representing at least a portion of the received patient data, wherein generating the graphic comprises:
      (a) using a plurality of consistent visual modification rules that convey additional information to the graphic;
      (b) rendering the second graphic as a dynamic isotype or disotype representing a base metric associated with the patient data, wherein rendering the disotype further comprises:
        (i) rendering the disotype with multiple dimensions of data wherein multiple attributes are associated with the base metric, wherein each attribute represents a separate dimension of data associated with the same base metric and each attribute is associated with a visual representation which is displayable in association with rendering the disotype, and,
        (ii) dynamically modifying a visual appearance of the disotype in response to comparison of a numerical value associated with the common metric to a threshold value associated with the base metric, wherein modifying the visual appearance of the disotype comprises modifying at least one of a color or a shape of the disotype; and
      (c) maintaining consistency of semantic meaning of at least one visual appearance of at least one of the attributes associated with the rendered disotype, including retaining the semantic meaning of the visual appearance as applied among different disotypes,
    add the graphic to a virtual patient chart, and
    transmit the virtual patient chart to a display device.

11. The system of claim 10, wherein the visual language engine comprises a transformative visualization module and a data normalization and aggregation module.

12. The system of claim 10, wherein the medical system is at least one of an electronic medical records system, a hospital information system, an electronic health record system, an imaging system, a digital imaging and communication in medicine (DICOM) system, a picture archiving system, a financial and billing system, a prescription management system, a laboratory system, a bed management system, a scheduling system, a single sign on (SSO) system, a communication/messaging system, and a molecular, nuclear and pathology lab system.

13. The system of claim 10, wherein the display device includes at least one of a handheld computing device, a smartphone, a tablet computer, a wearable computing device, a smart watch, a glasses-type computing device, a fixed display, a desktop workstation, a wall mounted monitor, a display that is integral with a piece of equipment, an x-ray machine display, a portable device, a mobile workstation, and a holographic and head-up display device.

14. An apparatus, comprising:
  means for receiving data relating to a patient;
  means for generating a graphic representing at least a portion of the received patient data, wherein the generating means comprises:
    (a) means for using a plurality of consistent visual modification rules that convey additional information to the graphic;
    (b) means for rendering the graphic as a dynamic isotype or disotype representing a base metric associated with the patient data, wherein the rendering means further comprises:
      (i) means for rendering the disotype with multiple dimensions of data wherein multiple attributes are associated with the base metric, wherein each attribute represents a separate dimension of data associated with the same base metric and each attribute is associated with a visual representation which is displayable in association with rendering the disotype, and, (ii) means for dynamically modifying a visual appearance of the disotype in response to comparison of a numerical value associated with the common metric to a threshold value associated with the base metric, wherein modifying the visual appearance of the disotype comprises modifying at least one of a color or a shape of the disotype; and (c) means for maintaining consistency of semantic meaning of at least one visual appearance of at least one of the attributes associated with the rendered disotype, including retaining the semantic meaning of the visual appearance as applied among different disotypes; and means for displaying the graphic on a virtual patient chart.

15. The apparatus of claim 14, further comprising means for receiving data relating to at least one piece of medical equipment.

16. A non-transitory computer readable medium including software for causing a processor to:

receive data relating to a patient;

generate a graphic representing at least a portion of the received patient data, wherein the generating comprises:

(a) using a plurality of consistent visual modification rules that convey additional information to the graphic;

(b) rendering the graphic as a dynamic isotype or disotype representing a base metric associated with the patient data, wherein rendering the disotype further comprises:

(i) rendering the disotype with multiple dimensions of data wherein multiple attributes are associated with the base metric, wherein each attribute represents a separate dimension of data associated with the same base metric and each attribute is associated with a visual representation which is displayable in association with rendering the disotype, and, (ii) dynamically modifying a visual appearance of the disotype in response to comparison of a numerical value associated with the common metric to a threshold value associated with the base metric, wherein modifying the visual appearance of the disotype comprises modifying at least one of a color or a shape of the disotype; and (c) maintaining consistency of semantic meaning of at least one visual appearance of at least one of the attributes associated with the rendered disotype, including retaining the semantic meaning of the visual appearance as applied among different disotypes; and enable display of the graphic on a virtual patient chart.

* * * * *